US009925321B2

(12) United States Patent
Surace et al.

(10) Patent No.: US 9,925,321 B2
(45) Date of Patent: Mar. 27, 2018

(54) APPARATUS FOR EXTRACORPOREAL BLOOD TREATMENT

(71) Applicant: GAMBRO LUNDIA AB, Lund (SE)

(72) Inventors: Alessandro Surace, Carpi (IT); Paolo Rovatti, Finale Emilia (IT)

(73) Assignee: Gambro Lundia AB, Lund (SE)

( * ) Notice: Subject to any disclaimer, the term of this patent is extended or adjusted under 35 U.S.C. 154(b) by 311 days.

(21) Appl. No.: 14/654,066

(22) PCT Filed: Dec. 16, 2013

(86) PCT No.: PCT/IB2013/060984
§ 371 (c)(1),
(2) Date: Jun. 19, 2015

(87) PCT Pub. No.: WO2014/097115
PCT Pub. Date: Jun. 26, 2014

(65) Prior Publication Data
US 2015/0343129 A1 Dec. 3, 2015

Related U.S. Application Data

(60) Provisional application No. 61/739,999, filed on Dec. 20, 2012.

(30) Foreign Application Priority Data

Dec. 20, 2012 (EP) .................................. 12198335

(51) Int. Cl.
*A61M 1/16* (2006.01)
*A61M 1/34* (2006.01)
*A61M 1/36* (2006.01)

(52) U.S. Cl.
CPC ............ *A61M 1/1613* (2014.02); *A61M 1/16* (2013.01); *A61M 1/1603* (2014.02);
(Continued)

(58) Field of Classification Search
CPC combination set(s) only.
See application file for complete search history.

(56) References Cited

U.S. PATENT DOCUMENTS

| 4,923,613 A | 5/1990 | Chevallet |
| 5,024,756 A | 6/1991 | Sternby |

(Continued)

FOREIGN PATENT DOCUMENTS

| CA | 2336923 | 1/2000 |
| DE | 19649775 | 6/1998 |

(Continued)

OTHER PUBLICATIONS

European Office Action—Application No. 12198335.7 dated May 17, 2016.

(Continued)

*Primary Examiner* — Dirk Bass
(74) *Attorney, Agent, or Firm* — K&L Gates LLP

(57) ABSTRACT

It is disclosed an apparatus for extracorporeal blood treatment (1) having a control unit (15) connected to an ultrafiltration device (20) and to a fluid preparation section (30) of fresh dialysis liquid. The control unit (15) is configured to receive measured values of the change of blood volume, the amount of ultrafiltration volume, and conductivity or to the concentration for at least one substance in the blood (BV $\%_{mes(t)}$; $U_{Fmes(t)}$, $WL_{mes(t)}$; $Cb_{mes(t)}$); the control unit (15) is also configured to receive prescription values for the same parameters and to control ultrafiltration and adjust conductivity in the fresh dialysis liquid based on the difference between said measured values and said prescription values.

32 Claims, 5 Drawing Sheets

(52) U.S. Cl.
CPC ........ *A61M 1/1605* (2014.02); *A61M 1/1611* (2014.02); *A61M 1/34* (2013.01); *A61M 1/341* (2014.02); *A61M 1/342* (2013.01); *A61M 1/3403* (2014.02); *A61M 1/3434* (2014.02); *A61M 1/3437* (2014.02); *A61M 1/3441* (2013.01); *A61M 1/3462* (2013.01); *A61M 1/3465* (2014.02); *A61M 1/36* (2013.01); *A61M 1/3607* (2014.02); *A61M 2205/3303* (2013.01); *A61M 2205/3317* (2013.01); *A61M 2205/3324* (2013.01); *A61M 2205/3331* (2013.01); *A61M 2205/3334* (2013.01); *A61M 2205/3379* (2013.01); *A61M 2205/3393* (2013.01); *A61M 2205/502* (2013.01); *A61M 2230/20* (2013.01); *A61M 2230/65* (2013.01)

(56) References Cited

U.S. PATENT DOCUMENTS

| | | | |
|---|---|---|---|
| 5,100,544 | A | 3/1992 | Polaschegg |
| 5,567,320 | A | 10/1996 | Goux et al. |
| 6,110,384 | A | 8/2000 | Goux et al. |
| 6,187,199 | B1 | 2/2001 | Rainer |
| 6,602,424 | B1 | 8/2003 | Kramer et al. |
| 2007/0131595 | A1 | 7/2007 | Jansson et al. |
| 2010/0004523 | A1 | 1/2010 | August et al. |
| 2014/0074008 | A1* | 3/2014 | Fontanazzi ............ A61M 1/34 604/5.04 |

FOREIGN PATENT DOCUMENTS

| | | |
|---|---|---|
| EP | 2380609 | 10/2011 |
| FR | 2713936 | 6/1995 |
| WO | 2012127298 | 9/2012 |

OTHER PUBLICATIONS

International Search Report—PCT/IB2013/060984—dated Jul. 7, 2014—3 pages.
European Search Report—EP Application No. 12198335.7-1651—dated May 23, 2013—7 pages.
Gotch et al., "A mechanistic analysis of the National Cooperative Dialysis Study (NCDS)", Kidney International, 1985, vol. 28, pp. 526-534.
International Search Report and Written Opinion dated Oct. 16, 2013, for related International Appln. No. PCT/IB2013/054875.
International Search Report—PCT/IB2013/059711—dated Apr. 14, 2014—5 pages.
Written Opinion—PCT/IB2013/059711—dated Apr. 14, 2014—8 pages.

* cited by examiner

APPARATUS FOR EXTRACORPOREAL BLOOD TREATMENT

CROSS-REFERENCE TO RELATED APPLICATIONS

The present application is a National Phase of International Application No. PCT/IB2013/060984, filed on Dec. 16, 2013, which claims priority to European Patent Application No. 12198335.7, filed Dec. 20, 2012, and U.S. Provisional Application No. 61/739,999, filed Dec. 20, 2012, the entire contents of each of which is incorporated herein by reference and relied upon.

The present invention relates to an apparatus for extracorporeal blood treatment having the ability to monitor parameters such as variation of blood volume, conductivity or concentration of the dialysis liquid and water removed from the patient and to thereby take appropriate control steps in order to deliver a comfortable treatment to the patient. The extracorporeal blood treatment apparatus may be for instance an hemodialysis or and hemodiafiltration apparatus.

Apparatus for extracorporeal blood treatment comprise at least one treatment unit (for example a dialyser or a hemofilter or an hemodiafilter or an ultrafilter or a plasma filter or a filtering unit of another type) having a semipermeable membrane which separates the treatment unit into two chambers. An extracorporeal blood circuit enables circulation of blood removed from a patient internally of the first chamber. At the same time, and typically in a counter-current direction with respect to the blood, a treatment fluid is made to circulate through an appropriate circuit in the second chamber of the treatment unit. This type of apparatus for blood treatment may be used for removal of excess solutes and fluids from the blood of patients suffering from kidney failure. A particular type of apparatus for blood treatment, known as hemofiltration or hemodiafiltration apparatus, comprises the presence of one or more infusion lines configured to send a replacement fluid into the extracorporeal blood circuit. The infusion line or lines may be connected upstream and/or downstream with respect to the treatment unit.

The above-described blood treatment apparatus may be controlled in various ways. For example, the apparatus may be volumetrically controlled, such as to have predetermined flow rates along the various fluid transport lines. Alternatively, the apparatus may be controlled such that the transmembrane pressure (herein indicated as TMP) follows a set value. Application WO2005IB01482 illustrates an apparatus and a process for setting the TMP value at a level which is such as to maximise the ultrafiltration flow rate and consequently the volume of fluid infused into the patient. This solution is advantageous as it maximises the ultrafiltration and infusion flow rates, thus improving convective exchange through the membrane and purification of blood from undesired particles.

Although the above-cited publication offers an advantageous procedure for setting TMP, extraction of fluid from a patient does not always correspond to a comfortable treatment for the patient. Also known are technical solutions, for example described in patent document EP778783, in which the apparatus for blood treatment is controlled such that two parameters, i.e. the variation in blood volume and the weight loss rate are maintained in a range of acceptability by contemporaneously controlling the conductivity of the dialysis liquid (i.e. the fluid in inlet to the second chamber of the treatment unit) and the weight loss rate. Although this type of control has led to benefits for the patient subjected to treatment and has enabled two targets to be reached with a single treatment, it should be noted that the use of the method of document EP778783 has essentially been limited to apparatus for hemodialysis.

Furthermore, it is known from WO2012/127298 an hemodiafiltration apparatus determining patient's blood volume, ultrafiltration flow rate, conductivity or concentration of a liquid crossing the dialysis line and/or the infusion line, and infusion flow rate ($Q_{INF}$). The apparatus comprises a control unit for controlling variation in blood volume and for imposing a transmembrane pressure (TMP) to values which enable maximising convective exchanges.

Although this last solution achieves integration convective clearance with a comfortable delivery of the treatment to the patient, the applicant has found ways to further improve the known systems.

SUMMARY

An aim of the present invention is to make available an apparatus for blood treatment which is able to integrate an efficient control on a plurality of prescription parameters such as total weight loss, blood volume change, and blood conductivity/concentration.

An additional aim of the present invention is to provide an apparatus which is able to implement an integrated control on a plurality of prescription parameters avoiding conflicts among controls and aimed at improving the comfort of the patient during treatment.

A further aim of the invention is to provide an apparatus which is able to actuate control relying as much as possible on the patient's feedback.

At least one of the above-indicated aims is substantially attained by an apparatus for blood treatment as in one or more of the appended claims.

At least one of the above objects is substantially reached by an apparatus according to one or more of the appended claims.

Apparatus and methods according to aspects of the invention and capable of achieving one or more of the above objects are here below described.

A 1st aspect concerns an apparatus for extracorporeal treatment of blood comprising:
- at least a treatment unit (2) having at least a first chamber (3) and at least a second chamber (4) separated from one another by a semipermeable membrane (5);
- at least a blood removal line (6) connected to an inlet port of the first chamber and configured to remove blood from a patient,
- at least a blood return line (7) connected with an outlet port of the first chamber and configured to return treated blood to the patient, the blood removal line (6), the blood return line (7) and the first chamber being part of an extracorporeal blood circuit (8);
- a dialysate circuit comprising:
  - at least a dialysis line (11) connected to the inlet port of the second chamber (4) and configured to convey fresh dialysis liquid to the second chamber (4), at least a fluid evacuation line (10) connected to an outlet port of the second chamber (4) and configured to discharge spent dialysis liquid exiting from the second chamber (4), and
  - a fluid preparation section connected to the dialysis line (11) and configured for adjusting the dialysis liquid conductivity, or the dialysis liquid concentration for at least one substance, in the fresh dialysis liquid;

at least one ultrafiltration device (20) connected to the dialysate circuit and configured for causing an ultrafiltration of fluid through the membrane from the first to the second chamber;

a control unit (15) connected to the ultrafiltration device (20) and to the fluid preparation section and configured to perform a control procedure aimed at:

controlling the ultrafiltration rate based on measures of the variation of blood volume over time and on the cumulated ultrafiltration volume, and controlling the composition of the fresh dialysis liquid based on measured values of the concentration of at least one substance in patient's blood or based on the patient's blood conductivity.

The patient's blood parameters used by the control procedure are measured in the blood circulating in the extracorporeal blood circuit.

In a 2nd aspect according to the 1st aspect the control procedure comprises a first control procedure which includes:

receiving measured values of:
a first parameter (BV $\%_{mes(t)}$) relating to the change of blood volume in the blood circulating in the extracorporeal blood circuit between start of the treatment and a respective treatment time instant (t), and
a second parameter related to the amount of ultrafiltration volume ($UF_{mes(t)}$; $WL_{mes(t)}$) cumulated until treatment time instant (t) from the start of the treatment, and receiving prescription values of the first parameter (BV $\%_{traj(t)}$), and of the second parameter ($UF_{traj(t)}$; $WL_{traj(t)}$) which have to be reached in the patient at treatment time instant (t);

controlling the ultrafiltration through said membrane, by acting on the ultrafiltration device (20), at least based on the measured values of the first and second parameters and on the prescription values of the same first and second parameters.

In a 3rd aspect according to any one of the preceding aspects, the control procedure includes a second control procedure comprising:

receiving a measured value of a third parameter ($Cb_{mes(t)}$) related to the dialysis liquid conductivity or to the concentration for at least one substance in the blood circulating in the extracorporeal blood circuit at a respective time instant (t) during treatment;

receiving a prescription value of the third parameter ($Cb_{traj(t)}$) to be reached in the patient at the time instant (t);

controlling the fluid preparation section to adjust dialysis liquid conductivity ($C_D$), or the dialysis liquid concentration of at least one substance ($Na_D$), in the fresh dialysis liquid flowing in the dialysate line at least based on said measured value ($Cb_{mes(t)}$) and on said prescription value for the third parameter ($Cb_{traj(t)}$).

In a 4th aspect according to the preceding aspect, the step of receiving a measured value of the third parameter takes place by measuring an in-vivo value of the third parameter ($Cb_{mes(t)}$), namely of the extracorporeal patient's blood concentration or conductivity.

In a 5th aspect according to the 4th aspect, the measuring of the in-vivo value comprises commanding execution of a measurement task including the following steps:

causing fresh treatment liquid to flow in the preparation line (19) to the secondary chamber (4) with the dialysis liquid conductivity, or to the dialysis liquid concentration for at least one substance, being at a baseline ($Cd_{set}$) set value which is either constant or varying in a known manner over time;

causing spent liquid to flow out of the secondary chamber (4) into the spent dialysate line (13);

causing an upstream variation to the dialysis liquid conductivity, or to the dialysis liquid concentration for at least one substance, ($Cd_{in}$) in the fresh treatment liquid with respect to said prescription baseline thereby causing a corresponding and timely delayed downstream variation to the dialysis liquid conductivity, or to the dialysis liquid concentration for at least one substance, ($Cd_{out}$) in the spent liquid flowing in the spent dialysate line (13);

measuring one or more values taken by said downstream variation of the dialysis liquid conductivity or dialysis liquid concentration for at least one substance ($Cd_{out}$) in the spent liquid;

determining the measured value of the third parameter ($Cb_{mes(t)}$) related to the blood conductivity or to the concentration for at least one substance in the blood, by comparing said one or more measured values taken by said downstream variation with one or more values taken by said upstream variation.

In a 6th aspect according to any one of the preceding aspects, the control unit (15) is configured to repeat the control procedure, e.g. the first control procedure and the second control procedure, at a plurality of regular time intervals during treatment such as to match, as closely as possible, the measured values of said first, second and third parameters to the respective prescription values.

In a 7th aspect according to any one of the preceding aspects from the 2nd to the 6th, the control unit (15) is configured to repeat the first control procedure as frequently as the second control procedure.

In a 8th aspect according to any one of the preceding aspects from the 2nd to the 6th, the control unit (15) is configured to repeat the first control procedure more frequently than the second control procedure.

In a 9th aspect according to any one of the preceding aspects from the 4th to the 8th, the control unit (15) is configured to repeat the first control procedure at least once every n minutes, and to repeat the measurement task and the second control procedure no more than once every m minutes, with n being an integer<than ½ m In a 10th aspect according to the preceding aspect wherein n is comprised between 1 and 5 and m is comprised between 10 and 30.

In a 11th aspect according to any one of the preceding aspects from the 4th to the 6th, the control unit (15) is configured to repeat the measurement task less frequently than the first control procedure thereby receiving the measured values of the third parameter ($Cb_{mes(t)}$) less frequently than the measured values (BV $\%_{mes(t)}$, $UF_{mes(t)}$; BV $\%_{mes(t)}$, $WL_{mes(t)}$) of the first and second parameters.

In a 12th aspect according to the preceding aspect the control unit (15) is further configured to estimate values taken by the third parameter at time instants intermediate between two consecutive executions of the measurement task at least based on:

a mathematical model (M), representing kinetics of the solutes in a distribution volume in the patient, and
the measured values of the third parameter made at said two consecutive measurement tasks, thereby obtaining plurality of estimated values of the third parameter between each two consecutive actually measured values of the same third parameter.

In a 13th aspect according to any one of the preceding aspects from the 2nd to the 12th, the second control procedure comprises receiving the measured value of the first parameter (BV $\%_{mes(t)}$) relating to the change of blood volume in the blood circulating in the extracorporeal blood circuit between start of the treatment and treatment time instant (t), and receiving the prescription value of the first parameter (BV $\%_{traj(t)}$) to be reached in the patient at treatment time instant (t); wherein the controlling step in the second control procedure comprises controlling the fluid preparation section to adjust the dialysis liquid conductivity ($C_D$), or the concentration of at least one substance ($Na_D$), in the fresh dialysis liquid flowing in the dialysate line at least based on the measured values of the first and third parameters (BV $\%_{mes(t)}$; $Cb_{mes(t)}$) and on the prescription values of the first and third parameters (BV $\%_{traj(t)}$; $Cb_{traj(t)}$).

In a 14th aspect according to any one of the preceding aspects from the 2nd to the 13th, the control unit (15)—during execution of said step of controlling the fluid preparation section—is configured to:
verify if said measurement task is under execution and, in the affirmative, wait for termination at least said upstream variation to the dialysis liquid conductivity, or to the dialysis liquid concentration for at least one substance ($Cd_{in}$), in the fresh treatment liquid with respect to said prescription baseline, and only then allow the first control procedure to adjust the dialysis liquid conductivity, or the dialysis liquid concentration of at least one substance, in the fresh dialysis liquid flowing in the dialysate.

In other words, the control unit may be configured to interdict any intervention on the composition of the dialysis liquid on the part of any task other than the measurement task while the change in conductivity or concentration imposed on the fresh dialysis liquid made by the measurement task is taking place.

In a 15th aspect according to any one of the preceding aspects from the 2nd to the 14th, wherein the values of the third parameter used as measured values in the second control procedure comprise actually measured values obtained with execution of said measurement task and estimated values relating to time instants intermediate between two consecutive of the measurement task.

In a 16th aspect according to any one of the preceding aspects from the 2nd to the 15th, the control unit (15) is configured to:
receiving a value for total treatment time (T);
receiving prescription values of blood volume variation (BV $\%_{target}$), weight loss ($WL_{target}$) and blood conductivity or concentration for at least one substance in blood ($Cb_{target}$) to be reached at end of treatment time (T);
determining said prescription values of the first parameter (BV $\%_{traj(t)}$), of the second parameter ($UF_{traj(t)}$; $WL_{traj(t)}$) and of the third parameter ($Cb_{traj(t)}$) on the basis of the respective prescription values to be reached at the end of the treatment and on the treatment time value (T).

In a 17th aspect according to the preceding aspect, receiving a prescription of the blood conductivity or concentration for at least one substance in blood ($Cb_{target}$) to be reached at end of treatment time (T) comprises imposing that said prescription value of conductivity or concentration for at least one substance in blood ($Cb_{target}$) to be reached at end of treatment time (T) shall be equal to the value of the blood conductivity or concentration for at least one substance in blood at the beginning of the treatment, in particular as measured or as set by user.

In a 18th aspect according to any one of the preceding aspects from the 2nd to the 17th, the control unit (15) is configured to execute the measurement task at the beginning of the treatment to measure the value of the conductivity or concentration for at least one substance in blood at the beginning of the treatment.

In a 19th aspect according to any one of the preceding aspects from the 2nd to the 18th, the first control procedure comprises:
determining at instant (t) at least a first error parameter ($ERR\_BV\_UF_{(t)}$) on the basis of:
the difference between the measured value of the first parameter (BV $\%_{mes(t)}$) at the control instant (t) and a corresponding prescription value for the same first parameter (BV $\%_{traj(t)}$), and
the difference between a measured value of the second parameter ($UF_{mes(t)}$; $WL_{mes(t)}$) cumulated at the instant (t) and a corresponding prescription value for the same second parameter ($UF_{traj(t)}$; $WL_{traj(t)}$); and
controlling the ultrafiltration through said membrane, by acting on the ultrafiltration device (20), at least based on the value of said first error parameter.

In a 20th aspect according to any one of the preceding aspects from the 2nd to the 19th, the second control procedure comprises:
determining at least a second error parameter ($ERR\_BV\_Na_{(t)}$) on the basis of:
the difference between the value of the third parameter ($Cd_{mes(t)}$) at instant (t) and a corresponding prescription value for the same third parameter ($Cb_{traj(t)}$), and the difference between the measured value of the first parameter (BV $\%_{mes(t)}$) and a corresponding prescription value for the same first parameter (BV $\%_{traj(t)}$); and
controlling the fluid preparation section to adjust the dialysis liquid conductivity ($C_D$), or the dialysis liquid concentration of at least one substance ($Na_D$), in the fresh dialysis liquid flowing in the dialysate line at least based on the value of said second error parameter.

In a 21st aspect according to any one of the preceding aspects, the apparatus is further comprising at least one infusion line configured for the infusion of a replacement fluid and connected to the extracorporeal circuit, wherein the control unit (15) is further configured to execute a TMP setting procedure comprising:
receive measured values of a fourth parameter (UFR; $Q_{INF}$) related to the ultrafiltration rate through the membrane or to the infusion rate through said infusion line and measured values of a fifth parameter related to the transmembrane pressure (TMP)) across said membrane;
impose on a first value of the first parameter ($TMP_n$) a first increase ($\delta TMP_n$) such as to reach a second transmembrane pressure value ($TMP_{n+1}$);
determine a variation between the value of the fourth patameter ($\Delta UFR_{(n)}$; $\Delta Q_{INF(n)}$) measured at the first transmembrane pressure ($TMP_n$) and the value of the fourth patameter ($\Delta UFR_{(n+1)}$ $Q_{INF(n+1)}$) measured at the second transmembrane pressure value ($TMP_{n+1}$);
compare the fourth parameter value variation ($\Delta UFR_{(n)}$; $\Delta Q_{INF(n)}$) with a reference value and, if the value of said variation is greater than the reference value, imposing a second increase ($\delta TMP_{n+1}$) on the second transmembrane pressure in order to reach a third value of the transmembrane pressure value $TMP_{n+2}$;

repeating the above steps of the TMP setting procedure until a maximum or substantially maximum TMP value is reached;

setting said TMP maximum or substantially TMP maximum or a predetermined fraction thereof as set value for the TMP in the course of at least a time interval during treatment.

In a 22nd aspect according to any one of the preceding aspects, the apparatus comprises at least a sensor active on the extracorporeal circuit and configured for detecting the variation (BV %) of the blood volume of the patient blood and configured to send to the control unit signals related to said variation of blood volume for the determination of the first parameter value.

In a 23rd aspect according to any one of the preceding aspects, the apparatus comprises at least a sensor active at least on the evacuation line and configured for determining the ultrafiltration rate (UFR) across the membrane, for the calculation of said second parameter value.

In a 24th aspect according to any one of the preceding aspects, the apparatus comprises at least a sensor active on the dialysis line (11) and configured for detecting dialysis liquid conductivity, or dialysis liquid concentration for at least one substance (Cd; Na), of the liquid crossing the dialysis line.

In a 25th aspect according to any one of the preceding aspects, the apparatus comprises at least a sensor configured for determining an infusion rate ($Q_{INF}$) of the replacement fluid crossing the infusion line.

In a 26th aspect according to any one of the preceding aspects, the apparatus comprises at least a sensor configured for determining a transmembrane pressure (TMP) between the first and the second chamber. In reality a plurality of sensors may be used as described in the corresponding section of the detailed description.

In a 27th aspect according to any one of aspects from the 22nd to the 26th the above sensors are connected to the control unit (15).

A 28th aspect concerns a method for controlling an extracorporeal treatment of blood, for instance an extracorporeal blood treatment of the type according to any one of the preceding aspects, comprising:

extracting blood from a patient using an extracorporeal circuit including a blood treatment unit, controlling the ultrafiltration rate through a membrane of the blood treatment unit based on measures of the variation of blood volume over time and on the cumulated ultrafiltration volume, and controlling the composition of the fresh dialysis liquid based on measured values of the concentration of at least one substance in patient's blood or based on the patient's blood conductivity.

The patient's blood parameters used by the above control steps are measured in the blood circulating in the extracorporeal blood circuit.

In a 29th aspect according to the 28th aspect the control method comprises a first control procedure which includes:

receiving measured values of:

a first parameter (BV $\%_{mes(t)}$) relating to the change of blood volume in the blood circulating in the extracorporeal blood circuit between start of the treatment and a respective treatment time instant (t), and a second parameter related to the amount of ultrafiltration volume ($UF_{mes(t)}$; $WL_{mes(t)}$) cumulated until treatment time instant (t) from the start of the treatment, and receiving prescription values of the first parameter (BV $\%_{traj(t)}$), and of the second parameter ($UF_{traj(t)}$; $WL_{traj(t)}$) which have to be reached in the patient at treatment time instant (t);

controlling the ultrafiltration through said membrane at least based on the measured values of the first and second parameters and on the prescription values of the same first and second parameters.

In a 30th aspect according to any one of the preceding two aspects, the control procedure includes a second control procedure comprising:

receiving a measured value of a third parameter ($Cb_{mes(t)}$) related to the blood conductivity or to the concentration for at least one substance in the blood circulating in the extracorporeal blood circuit at a respective time instant (t) during treatment;

receiving a prescription value of the third parameter ($Cb_{traj(t)}$) to be reached in the patient at the time instant (t);

adjusting dialysis liquid conductivity ($C_D$), or dialysis liquid concentration of at least one substance ($Na_D$), in the fresh dialysis liquid flowing in a dialysate line connected to the blood treatment unit at least based on said measured value ($Cb_{mes(t)}$) and on said prescription value for the third parameter ($Cb_{traj(t)}$).

In a 31st aspect according to the preceding aspect, the step of receiving a measured value of the third parameter takes place by measuring an in-vivo value of the third parameter ($Cb_{mes(t)}$), namely of the extracorporeal patient's blood concentration or conductivity.

In a 32nd aspect according to any one of the preceding aspects from the 28th to the 31st, the second control procedure comprises receiving the measured value of the first parameter (BV $\%_{mes(t)}$) relating to the change of blood volume in the blood circulating in the extracorporeal blood circuit between start of the treatment and treatment time instant (t), and receiving the prescription value of the first parameter (BV $\%_{traj(t)}$) to be reached in the patient at treatment time instant (t); wherein the controlling step in the second control procedure comprises controlling the dialysis liquid conductivity ($C_D$), or the dialysis liquid concentration of at least one substance ($Na_D$), in the fresh dialysis liquid flowing in the dialysate line at least based on the measured values of the first and third parameters (BV $\%_{mes(t)}$; $Cb_{mes(t)}$) and on the prescription values of the first and third parameters (BV $\%_{traj(t)}$; $Cb_{traj(t)}$).

DESCRIPTION OF THE DRAWINGS

The invention will be described with the aid of the figures of the drawings, by way of non-limiting example, which illustrate some aspects of the invention.

In particular.

DETAILED DESCRIPTION

Figure 1:
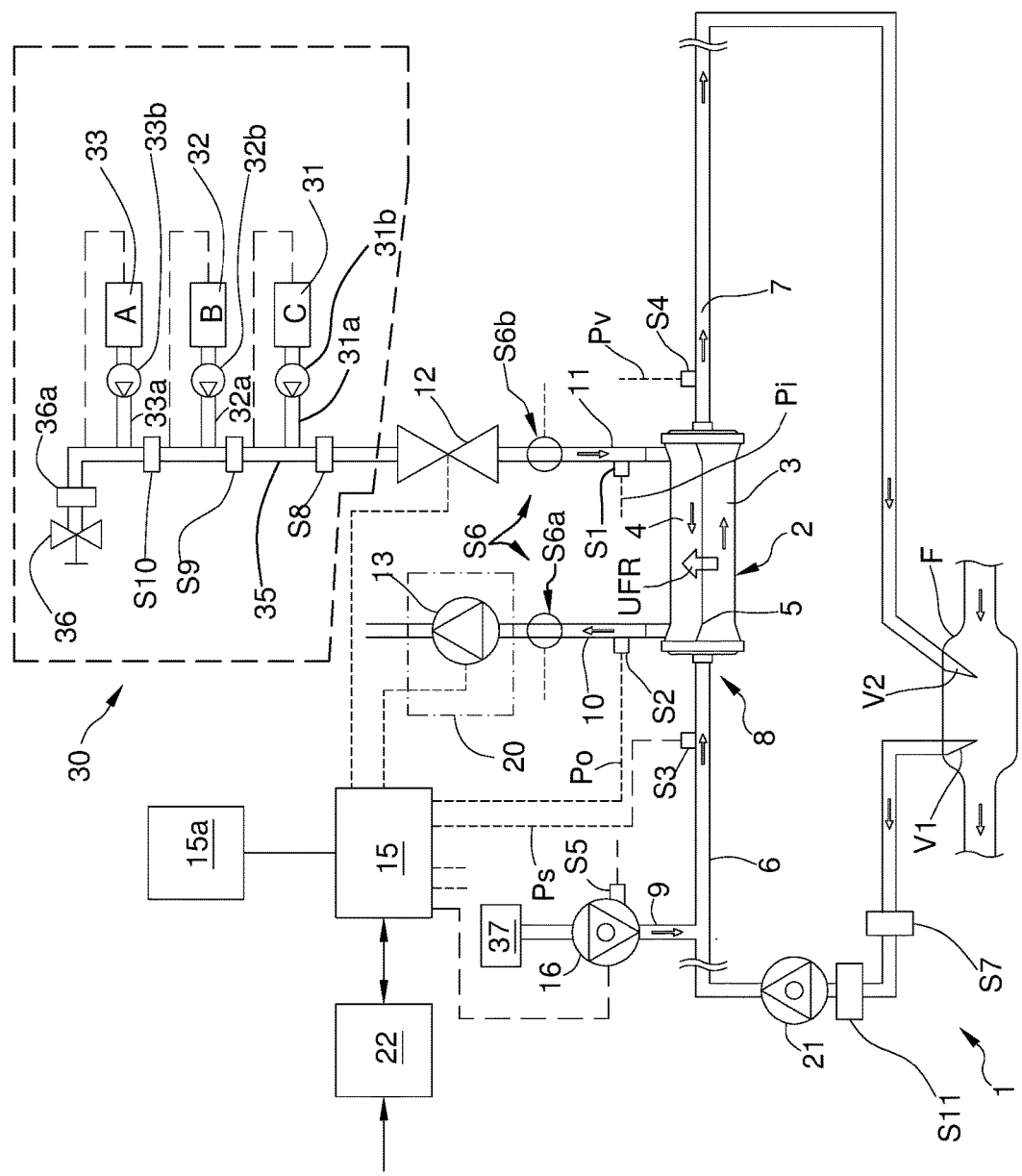
FIG. 1 is a schematic illustration of a first example of a blood treatment apparatus of the invention.
Figure 2:
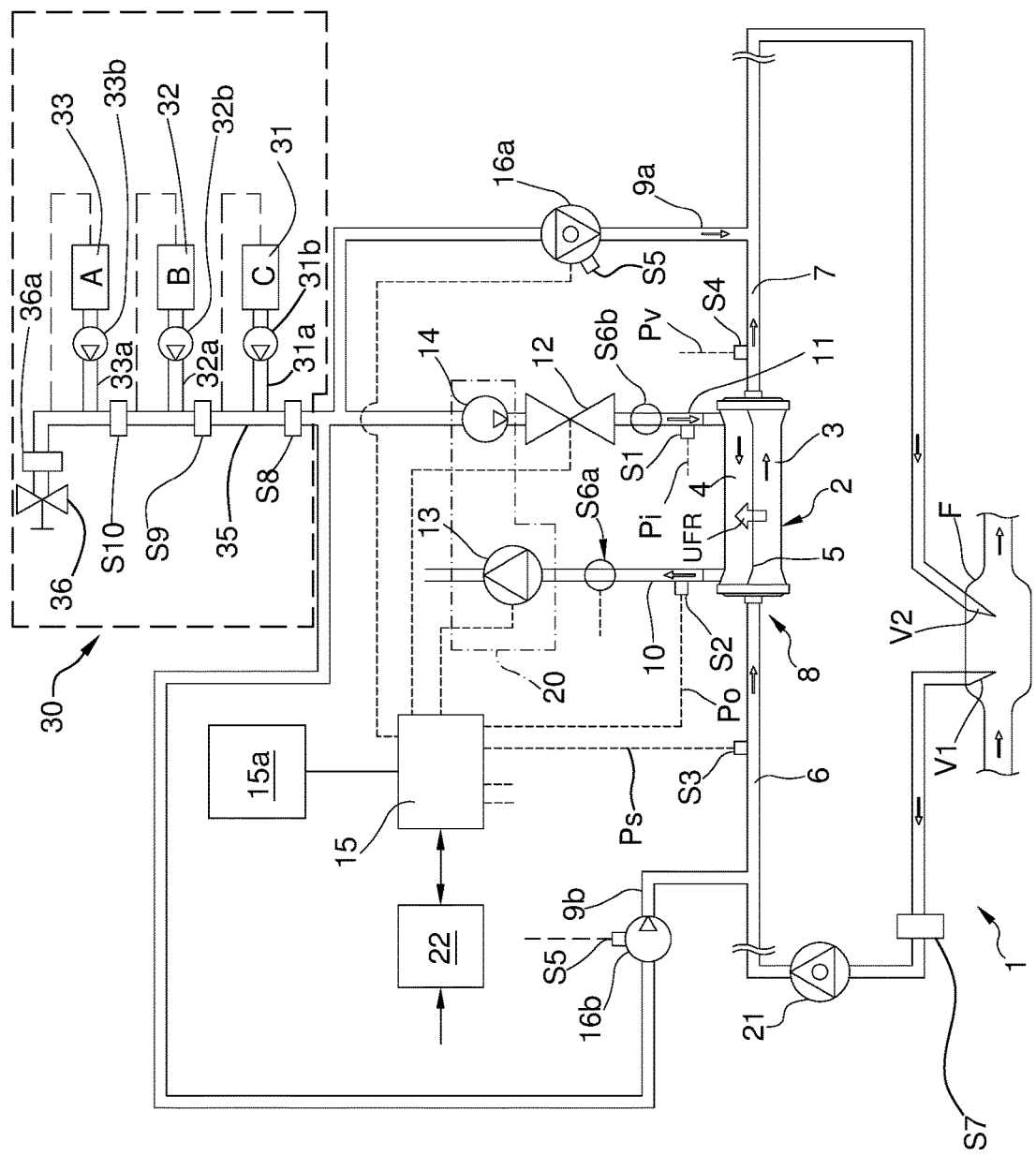
FIG. 2 is a schematic view of a second example of a blood treatment apparatus of the invention.

The following description relates to examples of extracorporeal blood treatment apparatus, such as for instance an hemodialysis or an hemodiafiltration apparatus, implementing aspects of the present invention. FIGS. 1 and 2 are non limiting examples schematically showing two possible embodiments of hemodiafiltration apparatus suitable for implementing aspects of the present invention.

With reference to FIGS. 1 and 2, reference numeral 1 denotes in its entirety an apparatus for extracorporeal blood treatment. The apparatus 1 comprises at least one treatment unit 2, for example a hemofilter or a hemodiafilter, having at least one first chamber 3 and at least one second chamber 4 separated from one another by a semipermeable membrane 5.

A blood removal line 6 is connected with an inlet port of the first chamber 3 and is capable, in operating conditions of connection to a patient, to remove blood from a vascular access V1 inserted for example in a fistula F of the patient. A blood return line 7, connected to an outlet port of the first chamber, is configured to receive the treated blood from the treatment unit and to return the treated blood to a further vascular access V2 connected with the patient's fistula. Note that the configuration of the vascular access may be of any nature: for example a catheter, a port implanted in the patient, a cannula, a needle, etc. The blood removal line 6, the first chamber 3 of the treatment unit and the blood return line 7 to the patient in practice are part of an extracorporeal blood circuit 8 which, during the use of the apparatus 1, provides for the circulation of the blood externally of the patient's body when subjected to treatment.

In the example of FIG. 1, an infusion line 9 of a replacement fluid is connected to the blood removal line 6, upstream of the first chamber 3. Alternatively, the infusion line 9 might be connected to the return line 7, downstream of the first chamber 3. In the example of FIG. 2 an infusion line 9a is connected downstream of the unit 2 while an infusion line 9b is connected upstream of the unit 2. With reference both to the example of FIG. 1 and FIG. 2, note that further infusion lines may also be provided, for example connected downstream or upstream of the treatment unit. The apparatus 1 further comprises a dialysate circuit comprising at least one fluid evacuation line 10 connected with an outlet port of the second chamber 4 for receiving at least a fluid filtered across the semipermeable membrane. In the examples of FIGS. 1 and 2, the dialysate circuit also includes a dialysis line 11 for supplying a fresh treatment fluid at the inlet to the second chamber 4; a fluid check organ 12 may be used to selectively enable or inhibit a passage of fluid across the dialysis line 11, according to whether it is desired, or not, to have a purification by diffusive effect internally of the treatment unit.

The apparatus 1 of both FIG. 1 and FIG. 2 comprises sensors (S1, S2, S3, S4, S5, S6, S7, S8, S9, S10) for determining the values assumed during treatment by certain parameters described herein below in greater. Of course other sensors may also be present in the apparatus 1.

Transmembrane Pressure (TMP)

During treatment it is necessary to move fluid and undesired particles from the first chamber 3 towards the second chamber 4 of the treatment unit 2. The fluid and particle movement creates a transmembrane pressure which is defined as the mean pressure applied on the side of the first chamber towards the side of the second chamber. The transmembrane pressure (hereinafter denoted in abbreviated form as TMP) may be practically determined in various modes. For example, an estimate of the transmembrane pressure TMP may be calculated as follows.

1) In a case in which (see FIGS. 1 and 2) four pressure sensors are present, of which one S1 is on the supply line 11, another S2 on the evacuation line 10, another S3 on the blood removal line 6 and a fourth S4 on the return line 7, an estimate of the TMP value may be determined by the control unit 15 using the pressure signals coming from sensors from S1 to S4 adopting the formula:

$$TMP = \frac{Ps + Pv}{2} - \frac{Pi + Po}{2}$$

where:
Pi is the pressure detected by sensor S1
Po is the pressure detected by sensor S2
Ps is the pressure detected by sensor S3
Pv is the pressure detected by sensor S4

2) In a case where the apparatus includes three pressure sensors, of which one S2 is on the evacuation line 10, another S1 on the dialysis line 11 and another S4 of the return line 7, an estimate of the TMP value may be determined by the control unit 15, using the pressure signals coming from said three sensors with the formula:

$$TMP = Pv - \frac{Pi + Po}{2}$$

where:
Po is the pressure detected by sensor S2
Pi is the pressure detected by sensor S1
Pv is the pressure detected by sensor S4

3) Finally, in a case the apparatus includes two pressure sensors, of which one is on the evacuation line 10 and one on the return line 7, an estimate of the TMP value may be determined by the control unit 15 using the pressure signals coming from the sensors S2 and S4 with the formula:

$$TMP = Pv - Po$$

where:
Po is the pressure detected by sensor S2
Pv is the pressure detected by sensor S4

Of course the above formulas are exemplifying only and other sensors and formulas may be adopted for determining the TMP.

Infusion Flow Rate ($Q_{INF}$)

The apparatus may comprise a sensor S5 of infusion flow rate $Q_{INF}$ of the replacement fluid through the infusion line 9 or the infusion lines 9a, 9b. The sensor or sensors S5 for detecting the flow may in practice be volumetric sensors, mass sensors such as for example Coriolis sensors, weight sensors such as for example scales, pump revolution sensors or sensors of still other types: as the type of sensors usable is not material to the present invention and since the techniques and the sensors for detecting absolute or differential flow values are known and within the experience of the expert person in the field, no further details provided.

In the case illustrated in FIGS. 1 and 2, the infusion flow rate sensors comprise sensors S5 configured to determine the number of revolutions of the infusion pumps, by sending a corresponding signal to the control unit 15 which is configured such as to calculate a flow rate along the respective infusion line based on the detected revolution rate and on certain calibration factors.

Ultrafiltration Flow Rate (UFR)

The apparatus 1 may further comprise at least one sensor S6 for detecting the ultrafiltration flow rate across the semipermeable membrane 5. For example, a flow sensor S6a may be present on the evacuation line 10 and a flow sensor S6a on the dialysis line 11 such as to provide the control unit 15 with the instant value of the respective flows and thus enable the control unit to calculate an instant value of the ultrafiltration flow rate as difference between the flow rate through the evacuation line 10 and the flow rate through the dialysis line 11. Alternatively, a differential sensor may be provided, active on the evacuation line and dialysis line and therefore able directly to provide a signal relating to the ultrafiltration flow rate. As a further alternative (not shown), an ultrafiltration line may be provided branching off the evacuation line 10: in this case the flow rate in the dialysis line 11 and in the evacuation line 10 downstream the branching off point may be kept balanced such that the ultrafiltration flow rate is identical to the flow rate through the ultrafiltration line which may be measured with an appropriate flow sensor (e.g. of the type as sensor S6) or by a scale. The sensor or sensors S6, S6a, S6b may in practice be volumetric sensors, mass sensors such as for example Coriolis sensors, weight sensors such as for example scales, pump revolution sensors, or sensors of yet another type: as the type of sensors usable is not material to the present invention and since the techniques and the sensors for detecting absolute or differential flow values are known and within the experience of the expert person in the field, no further details are included in the present description.

Weight Loss Rate (WLR)

The weight loss rate WLR may be measured by subtracting the infusion rate (for example as measured above) from the ultrafiltration flow rate UFR (for example as described above) because the three just mentioned rates are linked by the relationship UFR=$Q_{INF}$+WLR. In other words, having sensors S6 and S5 available, the control unit 15 may be programmed to derive (e.g.: to mathematically calculate) the weight loss rate WLR. As a further alternative, a sensor may be provided which is able to provide a signal which gives the weight loss rate: for example a sensor able to differentially measure the rate taken from the evacuation line and to subtract the flow rate through the dialysis line and/or the flow rate or rates through the infusion line or lines. The sensor may materially be a mass flow sensor (for example a Coriolis sensor), a volumetric sensor, an electromagnetic sensor, a weight sensor (such as a scales able to weigh bags of fluid) or another type of sensor.

Blood Volume

The apparatus 1 comprises a sensor S7 for detecting the variation of blood volume (BV %) or a parameter from which the variation in blood volume may be calculated in relation to the blood of a patient subjected to treatment. The blood volume variation sensor may for example be an optical sensor, able to detect a variation in the optical properties of the blood crossing a calibrated portion of tube. For example, a blood volume variation detection may comprise calculating, by control unit 15, a percentage variation of the blood volume circulating in the patient (BV %) from start of hemodialysis treatment (or hemofiltration, or hemodiafiltration) based on the measurement of the concentration of hemoglobin in the blood, according to the known formula:

$$BV\% = (HGB_0/HGB_t) - 1,$$

where $HGB_0$ represents the concentration of hemoglobin at start of treatment and $HGB_t$ the concentration of hemoglobin at time t in which BV % is calculated.

The hemoglobin concentration may be calculated based on the variation of optic absorbance at a predetermined wavelength, detected by an optical sensor, of the blood flowing in the blood removal line 6. The optical sensor is for example associated to a tract of tube having the appropriate optical properties which have previously measured or which are known. Of course the values of HGB may alternatively be measures with other techniques such as measuring other blood properties (e.g.: capacitance, impedance), without departing from the scope of the present invention.

Weight Loss

The apparatus 1 may also determine the weight loss over a time period, for example from start of treatment up to a certain instant t: for example the control unit 15 may be programmed to integrate the weight loss rate WLR over the time. Alternatively, a weight loss sensor may be provided, for example a sensor destined to detect the variation in overall weight of a patient during treatment, or a sensor destined to directly detect the overall weight of the net fluid extracted from a patient.

Conductivity or Concentration

The apparatus 1 further comprises at least one sensor S8 configured for sensing conductivity of the dialysis liquid or sodium concentration (or concentration of another substance that is to be monitored) of the dialysis liquid flowing through the dialysis line 11. For example, the conductivity or concentration sensor S8 may be located immediately downstream of a device for regulating a composition of dialysis liquid and/or replacement liquid, which will be more fully described in the following.

Ultrafiltration Device

The apparatus 1 further comprises an ultrafiltration device 20 for regulating ultrafiltration or transmembrane pressure TMP between the first and the second chamber of the treatment unit. The ultrafiltration device 20 is connected to the control unit 15 and active on at least one of the extracorporeal circuit and the dialysate circuit. The first regulating device may comprise: a pump 13 located on the fluid evacuation line 10, or two blood pumps located one upstream and one downstream of the filter unit 2 and controlled at different speeds, or a pump 13 in the dialysis line 11 and a pump 14 in the evacuation line 10 which are controlled at different speeds so as to generate a net ultrafiltration flow rate across the membrane. Of course, other combinations of one or more pumps or valves appropriately arranged on the blood line or fluid evacuation line or dialysate line are possible. In the example illustrated in FIGS. 1 and 2, the device 20 comprises an ultrafiltration pump 13 operating on the evacuation line and able to pull fluid from the second chamber. In the example of FIG. 2, a treatment fluid supply pump 14 operating on the dialysate line is also present: in this case the ultrafiltration device 20 therefore comprises both the ultrafiltration pump and the supply pump, which are differentially controlled such as to create an ultrafiltration flow UFR across the membrane. The control unit 15 may command the ultrafiltration device 20 (in the example of FIGS. 1 and 2, the pumps 13 and 14) such that the TMP measured value corresponds to the set value for the TMP. In this case, the control unit acts continuously or periodically on the ultrafiltration device 20 such that, instant by instant, the measured TMP measured corresponds set TMP value prescribed for that instant (TMP pressure control). In this way, the ultrafiltration flow rate UFR across the membrane and thus the quantity of fluid removed from the blood present in the first chamber is a function of the imposed TMP. Alternatively, the control unit 15 may be programmed such that the ultrafiltration flow rate UFR follows one or more set values for ultrafiltration flow rate (volumetric control): in this case, the TMP will be variable and the control unit will act on the ultrafiltration device 20 such as to maintain the ultrafiltration flow rate constantly close or equal to a reference value or values prescribed or calculated for the UFR.

Fluid Preparation Section

The apparatus 1 may further comprise a fluid preparation section 30 for regulating a composition of the dialysis liquid and/or the replacement liquid. In the example of FIG. 1 and FIG. 2, the fluid preparation section 30 comprises one, two or more containers of concentrate 31, 32, 33 located on respective injection lines 31a, 32a, 33a which are configured to supply substances such as electrolytes, buffer agents or other towards a preparation line 35 of the liquid located upstream of the dialysis line 11. The concentrate containers may comprise concentrates in the liquid state or solid state, for example powder. Injection pumps 31b, 32b, 33b may be present on the injection lines to circulate fluid along the respective injection line towards the preparation line 35 which collects the liquid, for example water, from a source 36. The source 36 may comprise tap water or a source of ultra-pure liquid or other: the water collected from the source and possibly subjected to filtering stages 36a (not detailed as known and not relevant to the present invention) is provided with the necessary substances by the injection lines of the fluid preparation section 30. The concentration or conductivity sensor S8 is able to provide the control unit 15 with a signal relative to dialysis liquid conductivity or dialysis liquid concentration of a predetermined substance (for example sodium) of the fluid exiting line 35 and entering dialysis line 11. Note that, optionally, further concentration or conductivity sensors S9 and S10 may be located on the line 35, respectively in correspondence of segments of line 35 extending between the injection points of injection lines 33a and 32a and between the injection points of injection lines 32a and 31a. The control unit may act on the device 30 and in particular on the pumps 31b, 32b, 33b in order to regulate the conductivity Cd or concentration, for example of sodium $Na_D$, of the liquid flowing into the dialysis line 11. In the example of FIG. 1, the infusion line 9 collects the fluid from an independent source 37 (for example a bag containing replacement fluid) which is separate and distinct with respect to the source 36, while the preparation line 35 exclusively supplies dialysis line 11. In the example of FIG. 2, the infusion lines 9a and 9b, as well as the dialysis liquid line collect fluid from the supply line 35, such that the composition of the dialysis liquid through line 11 and through infusion lines 9a, 9b is the same.

Control Unit

As already indicated the apparatus according to the invention makes use of at least one control unit 15. This control unit 15 may comprise a digital processor (CPU) with associated memory 15a (or memories), an analogical type circuit, or a combination of one or more digital processing units with one or more analogical processing circuits. In the present description and in the claims it is indicated that the control unit 15 is "configured" or "programmed" to execute certain steps: this may be achieved in practice by any means which allow configuring or programming the control unit 15. For instance, in case of a control unit 15 comprising one or more CPUs, one or more programs are stored in an appropriate memory: the program or programs containing instructions which, when executed by the control unit 15, cause the control unit 15 to execute the steps described and/or claimed in connection with the control unit 15. Alternatively, if the control unit 15 is of an analogical type, then the circuitry of the control unit 15 is designed to include circuitry configured, in use, to process electric signals such as to execute the control unit 15 steps herein disclosed or claimed.

As illustrated in the examples of FIGS. 1 and 2, the control unit is connected with the ultrafiltration device 20, with the preparation section 30, with a user interface 22, with the sensors S1 to S10 described above and with the various actuator organs (blood pump 21, infusion pumps 16, 16a, 16b, ultrafiltration pump 13, dialysis pump 11 and valve 12) located along the lines 7, 8, 9, 9a, 9b, 10, 11 and is configured or programmed to perform the procedures described herein.

In an aspect of the invention (see FIGS. 3 and 4), the control unit 15 is programmed or configured such as to perform, at control instants t temporally one after another (for example the instants t may be temporally equidistant), a control procedure 50 comprising the steps described herein below. The control unit may also be programmed to perform, in combination with the control procedure, a TMP setting procedure: the setting sequence of the TMP and the control procedure are coordinated by the control unit such as to prevent negative interactions.

Figure 3:
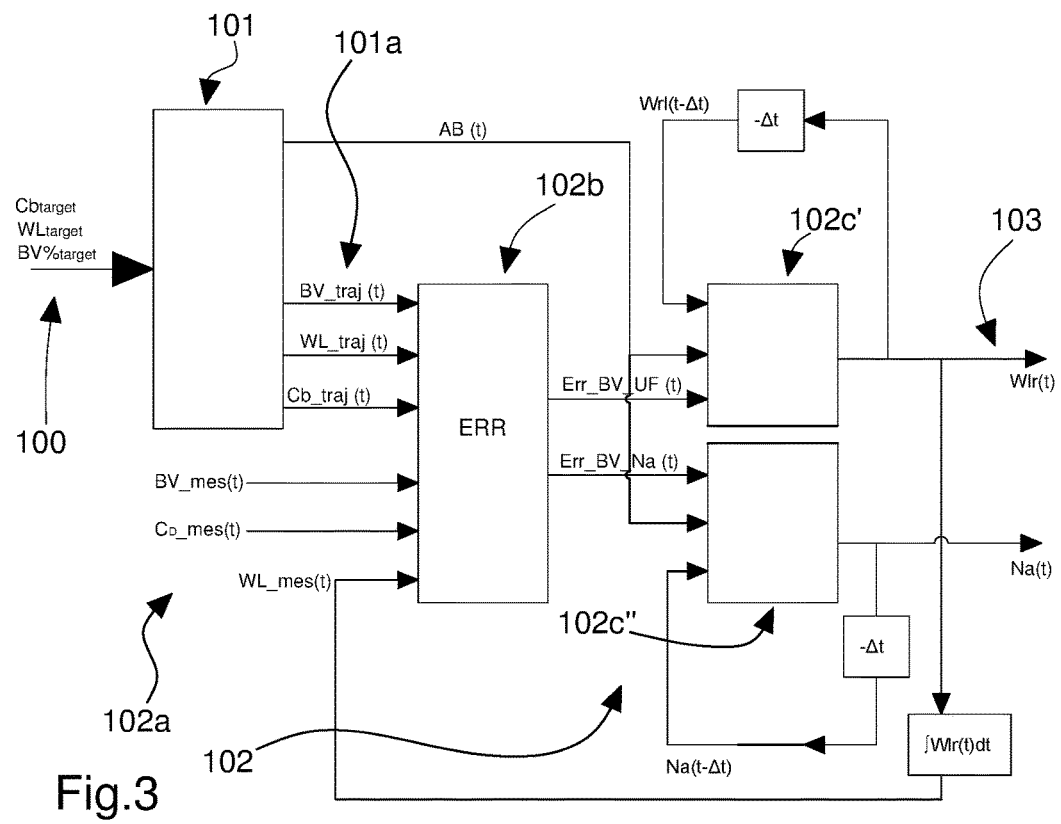
FIG. 3 is a block diagram relating to the, e.g. periodic, calculation of control values for the ultrafiltration rate/weight loss rate and for the concentration/conductivity of the dialysis liquid which the control unit makes and then imposes on the apparatus.
Figure 4:
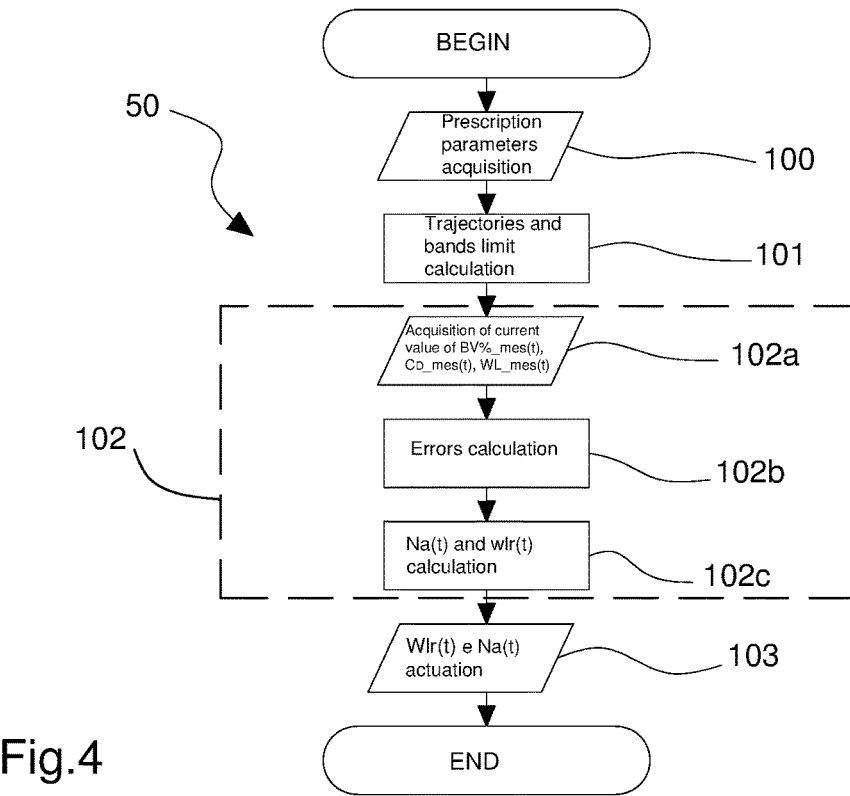
FIG. 4 is a flow diagram showing a control procedure according to the invention, which may be carried out by the control unit of an apparatus, for example, of the type illustrated in FIG. 1 or FIG. 2.

Referring to FIGS. 3 and 4 it is here below described the calculation of control values for the ultrafiltration rate/weight loss rate and for the concentration/conductivity. In a first step 100, the control procedure comprises receiving, for example via the interface 22, prescription values of the blood volume variation $BV\%_{target}$, of the weight loss $WL_{target}$, and of the blood conductivity $Cb_{target}$ or sodium concentration $Na_{target}$ to be achieved in the patient's blood at a predetermined treatment time T. For example, the user interface 22 may enable entering of said prescription values and selection of a treatment time value T within which the prescription values have to be achieved. Thereafter, at step 101, the control procedure on the basis of the prescription values and the treatment time value T, determines respective target profiles which describe the desired progression over time (or trajectory) of the variation of:

a first parameter $BV\%_{traj(t)}$ relating to the change of blood volume in the blood circulating in the extracorporeal blood circuit between start of the treatment and a respective treatment time instant (t); the first parameter may in practice be the change in blood volume taking place between the treatment start and instant t in the blood circulating in the extracorporeal blood circuit;

a second parameter $UF_{traj(t)}$, $WL_{traj(t)}$ related to the amount of ultrafiltration volume or weight loss volume $UF_{mes(t)}$; $WL_{mes(t)}$ cumulated until treatment time instant (t) from the start of the treatment; the second parameter may be either the cumulated ultrafiltration volume or the cumulated weight loss volume (note that ultrafiltration volume and weight loss volume have coincident values in those case where there is pure hemodialysis and thus no infusion of fluid in the extracorporeal blood circuit or directly into the patient);

a third parameter $Cb_{traj(t)}$ related to the conductivity or to the concentration for at least one substance in the blood circulating in the extracorporeal blood circuit at a respective time instant (t) during treatment; in practice the third parameter may be the concentration of sodium in the blood circulating in the extracorporeal circuit at time t.

In summary, the target profiles provide, at each time instant, the prescription values of the first parameter $BV\%_{traj(t)}$, of the second parameter $UF_{traj(t)}$, $WL_{traj(t)}$ and of the third parameter $Cb_{traj(t)}$. At step 101, the control unit may also be configured to calculate the allowed bands AB(t) for each one of the first parameter $BV\%_{traj(t)}$, the second parameter $UF_{traj(t)}$, $WL_{traj(t)}$ and the third parameter $Cb_{traj(t)}$.

Note that—as an alternative to being calculated by the control unit on the basis of the respective prescription values to be reached at the end of the treatment and on the treatment time value T—said target profiles for the prescription values may be entered by a user or they may be pre-stored in a memory connected with the control unit.

It should be noted that the blood conductivity $Cb_{target}$ or concentration for at least one substance in blood $Na_{target}$ to be reached at end of treatment time T may be calculated based on an initial value for the same parameter. For instance, the control unit 15 may be configured for imposing that said prescription value of conductivity $Cb_{target}$ or concentration for at least one substance $Na_{target}$ in blood to be reached at end of treatment time T shall be equal to the value of the conductivity or concentration for at least one substance in blood at the beginning of the treatment, in particular as measured or as set by user. In this case, the control unit may be configured to execute a measurement task (which is described in detail herein below) at the beginning of the treatment to measure the value of the conductivity or concentration for at least one substance in blood at the beginning of the treatment and then to impose that said measured value shall be equal to the target value.

Again with reference to FIGS. 3 and 4, at step 102, the control unit 15 is configured to execute two control procedures: the two control procedures are logically distinct but may be implemented in a single software task executed by the control unit or in a single circuit block part of the control unit. When executing the first control procedure, the control unit 15 is configured to:

receive (step 102a) measured values of the first parameter $BV\%_{mes(t)}$ relating to the change of blood volume in the blood circulating in the extracorporeal blood circuit between start of the treatment and a respective treatment time instant t, receive (step 102a) measured values of the second parameter related to the amount of ultrafiltration volume $UF_{mes(t)}$ or $WL_{mes(t)}$ cumulated until treatment time instant t from the start of the treatment, receive (step 101a) prescription values of the first parameter $BV\%_{traj(t)}$, and of the second parameter $UF_{traj(t)}$ or $WL_{traj(t)}$ which have to be reached in the patient at treatment time instant t, control the ultrafiltration (step 103) through the membrane 5 of the treatment unit 2 by acting on the ultrafiltration device 20, at least based on the measured values of the first and second parameters (at instant t) and on the prescription values of the same first and second parameters (at instant t). In practice, the control unit may be programmed to control the ultrafiltration device 20 and to adjust it based on the discrepancy between the first and second parameter prescription values and the respective measured values.

When executing the second control procedure the control unit is configured to:

receive (step 102a) a measured value of the third parameter $Cb_{mes(t)}$ related to the conductivity or to the concentration for at least one substance in the blood circulating in the extracorporeal blood circuit at a respective time instant t during treatment;

receive (step 101a) the prescription value of the third parameter $Cb_{traj(t)}$ to be reached in the patient at the time instant t;

control (step 103) the fluid preparation section to adjust the conductivity $C_D$, or the concentration of at least one substance $Na_D$, in the fresh dialysis liquid flowing in the dialysate line at least as a function of said measured value $Cb_{mes(t)}$ and on said prescription value for the third parameter $Cb_{traj(t)}$. For instance the adjustment of the conductivity or concentration (e.g., Na concentration) in the fresh dialysis liquid may be made by the control unit based on the discrepancy between the prescription and the measured values (at instant t) for the third parameter.

In accordance with a more sophisticated alternative the second control procedure also uses the measured value of the first parameter $BV\%_{mes(t)}$ relating to the change of blood volume in the blood circulating in the extracorporeal blood circuit between start of the treatment and treatment time instant t, and the prescription value of the first parameter $BV\%_{traj(t)}$ to be reached in the patient at treatment time instant t. In this alternative, the second control procedure comprises controlling the fluid preparation section to adjust the conductivity $C_D$, or the concentration of at least one substance $Na_D$ in the fresh dialysis liquid flowing in the dialysate line at least based on the measured values of the first and third parameters $BV\%_{mes(t)}$, $Cb_{mes(t)}$ and on the prescription values of the first and third parameters $BV\%_{traj(t)}$, $Cb_{traj(t)}$ For instance the adjustment of the conductivity or concentration (e.g., Na concentration) in the fresh dialysis liquid may be made by the control unit as a function of the discrepancy between the prescription and the measured values (at instant t) for the third parameter and as a function of the discrepancy between the prescription and the measured values (at instant t) for the first parameter.

The step of receiving the measured value of the third parameter $Cb_{mes(t)}$ comprises commanding execution of a measurement task comprising the following steps:

causing fresh treatment liquid to flow in the preparation line (19) to the secondary chamber (4) with the conductivity, or to the concentration for at least one substance, being at a baseline ($Cd_{set}$) set value which is either constant or varying in a known manner over time;

causing spent liquid to flow out of the secondary chamber (4) into the spent dialysate line (13);

causing an upstream variation to the conductivity, or to the concentration for at least one substance, ($Cd_{in}$) in the fresh treatment liquid with respect to said prescription baseline thereby causing a corresponding and timely delayed downstream variation to the conductivity, or to the concentration for at least one substance, ($Cd_{out}$) in the spent liquid flowing in the spent dialysate line (13);

measuring one or more values taken by said downstream variation of the conductivity or concentration for at least one substance ($Cd_{out}$) in the spent liquid;

determining the measured value of the third parameter ($Cb_{mes(t)}$) related to the conductivity or to the concentration for at least one substance in the blood, by comparing said one or more measured values taken by said downstream variation with one or more values taken by said upstream variation.

In practice—in order to determine the conductivity or the concentration of a substance (such as Na, for example) in blood—any one of the procedures disclosed in the following publications may be adopted. Document EP 0547025 describes a method for determining the conductivity or concentration of a substance, such as sodium, in a patient's blood subjected to a dialysis treatment. This method also makes it possible to determine the dialysance D—for example for sodium—of the blood treatment unit or dialyzer used. The method comprises the steps of circulating a first and a second dialysis liquids having different sodium concentrations in succession through the second chamber of the blood treatment unit, measuring the conductivity of the first and second dialysis liquids upstream and downstream of the dialyzer, and computing the concentration of sodium in the patient's blood (or the dialysance D of the dialyzer for sodium) from the values of the conductivity of the liquid which are measured in the first and second dialysis liquids upstream and downstream of the dialyzer. Document EP 0658352 describes another method for the in vivo determination of dialysis parameters (including conductivity or concentration of a substance, such as sodium, in a patient's blood) which comprises the steps of: making at least a first and a second treatment liquids, having a characteristic (the conductivity, for example) associated with at least one of the parameters (the ion concentration of the blood, the dialysance D, the clearance K, Kt/V, for example) indicative of the treatment, flow in succession through the dialyzer, the value of the characteristic in the first liquid upstream of the exchanger being different from the value of the characteristic in the second liquid upstream of the dialyzer; measuring, in each of the first and second treatment liquids, two values of the characteristic, respectively upstream and downstream of the dialyzer; making a third treatment liquid flow through the dialyzer while the characteristic of the second liquid has not reached a stable value downstream of the dialyzer, the value of the characteristic in the third liquid upstream of the dialyzer being different from the value of the characteristic in the second liquid upstream of the dialyzer; measuring two values of the characteristic in the third liquid, respectively upstream and downstream of the dialyzer; and computing at least one value of at least one parameter indicative of the progress of the treatment from the measured values of the characteristic in the first, second and third treatment liquids. Another method for the in vivo determination of the dialysis parameters (including conductivity or concentration of a substance, such as sodium, in a patient's blood) which does not require taking measurements on blood samples is described in document EP 0920877. This method includes the steps of: making a treatment liquid flow through the exchanger, this treatment liquid having a characteristic which has an approximately constant nominal value upstream of the exchanger; varying the value of the characteristic upstream of the exchanger and then re-establishing the characteristic to its nominal value upstream of the exchanger; measuring and storing in memory a plurality of values adopted by the characteristic of the treatment liquid downstream of the exchanger in response to the variation in the value of this characteristic caused upstream of the exchanger; determining the area of a downstream perturbation region bounded by a baseline and a curve representative of the variation with respect to time of the characteristic; and computing the parameter indicative of the effectiveness of a treatment from the area of the downstream perturbation region and from the area of an upstream perturbation region bounded by a baseline and a curve representative of the variation with respect to time of the characteristic upstream of the exchanger.

Of course, any other procedure adapted for the in vivo determination of blood conductivity or concentration for one substance without blood sampling may equivalently be adopted. For instance document US 2001004523 describes a solution for continuously determining dialysance/clearance for one substance, conductivity/concentration in blood comprising the steps of: causing a succession of sinusoidal variations in the characteristic (Cd) a treatment liquid upstream of the exchanger, continuously storing in memory a plurality of values ($Cd_{in1}$ ... $Cd_{inj}$ ... $Cd_{inp}$) of the characteristic (Cd) upstream of the exchanger, measuring and continuously storing in memory a plurality of values ($Cd_{out1}$ ... $Cd_{outj}$ ... $Cd_{outp}$) adopted by the characteristic (Cd) downstream of the exchanger in response to the variations in the characteristic (Cd) which are caused upstream of the exchanger, computing—each time that a predetermined number of new values ($Cd_{outj}$) of the characteristic (Cd) downstream of the exchanger has been stored—said parameter (D, Cbin, K, Kt/V) from a first series of values ($Cd_{inj}$) of the characteristic (Cd) upstream of the exchanger, from a second series of values ($Cd_{outj}$) of the characteristic (Cd) downstream of the exchanger.

Irrespective of how in practice the measurement task is executed, it should be noted that the control unit 15 may be configured to repeat the first control procedure and the second control procedure at a plurality of regular time intervals during treatment such as to match, as closely as possible, the measured values of said first, second and third parameters to the respective prescription values. For instance the control procedures may be repeated every 15 minutes or every 30 minutes. Moreover, irrespective of the frequency, the two control procedures may take place substantially with reference to a same time instant or at distinct time instants: e.g. once the first control procedure has been completed the second control procedure may be initiated.

The control unit is configured to repeat the first control procedure more frequently than the second control procedure: for instance the first control procedure may be repeated at least once every n minutes, while the measurement task and the second control procedure are repeated no more than once every m minutes, with n being an integer<than ½ m. In accordance with one example n is comprised between 1 and 5 and m is comprised between 10 and 30. This allows the first control procedure to continuously execute the ultrafiltration adjustment to accomplish the targets of BV % and WL, while the adjustments on the composition of the dialysis liquid (which may disturb the patient and require significant measurement time) are less frequently repeated.

In the embodiment where the control unit is configured to repeat the measurement task less frequently than the first control procedure thereby receiving the measured values of the third parameter ($Cb_{mes(t)}$) less frequently than the measured values ($BV\%_{mes(t)}$, $UF_{mes(t)}$; $BV\%_{mes(t)}$, $WL_{mes(t)}$) of the first and second parameters, the control unit 15 may be further configured to estimate values taken by the third parameter at time instants intermediate between two consecutive executions of the measurement task at least based on a mathematical model M, representing kinetics of the solutes in a distribution volume in the patient, and the measured values of the third parameter made at said two consecutive measurement tasks. This allows to thereby obtaining a plurality of estimated values of the third parameter between each two consecutive actually measured values of the same third parameter. The estimated values may be used in place of the in vivo measured values if the second control procedure is executed more frequently then the measurement task: in other words if actually measured in vivo values of conductivity/concentration in blood Cb are not available when the second control procedure is executed, then the estimated values may be used. The mathematical model adopted is not relevant for the purpose of this description and any mathematical model M representative of kinetics of the solutes in the distribution volume in the patient V, e.g. according to a single-compartment model, may be used. The distribution volume V is determined for each patient on the basis of the weight loss objective $WL_{target}$, the total accumulated weight loss $WL_{(t)}$ and the volume of corporeal water TBW estimated for example on the basis of information such as age, sex, height and weight of the patient. For example, some example formulae for calculating the volume of corporeal water TBW are the following:

Input parameters: Sex, Height [cm], Weight [Kg], Age [years], Volume %
Output parameters: volume of corporeal water (TWB) [L]

Watson's Formula if Sex="Male", then $$TWB=2.447-(0.09516*Age)+(0.1074*Height)+(0.3362*Weight)$$

if Sex="Female", then $$TWB=-2.097+(0.1069*Height)+(0.2466*Weight)$$

Hume-Weyer's Formula if Sex="Male", then $$TWB=(0.194786*Height)+(0.296785*Weight)-14.012934$$

if Sex="Female", then $$TWB=(0.344547*Height)+(0.183809*Weight)-35.270121$$

Mellits-Cheek's Formula if Sex="Male" and Height≤132.7 cm, then $$TWB=-1.927+(0.465*Weight)+(0.045*Height)$$

if Sex="Male" and Height>132.7 cm, then $$TWB=-21.993+(0.406*Weight)+(0.209*Height)$$

if Sex="Female" e Height≤110.8 cm, then $$TWB=0.076+(0.507*Weight)+(0.013*Height)$$

if Sex="Female" e Height>110.8 cm, then $$TWB=-10.313+(0.252*Weight)+(0.154*Height)$$

Percentage Formula $$TWB=Weight*Volume\ \%/100$$

In accordance with a further aspect of the invention, during execution of the measurement task, the control unit may be configured to prevent changes in conductivity or concentration of the dialysis liquid imposed by any task or procedure other than the measurement task. In particular—during execution of said step of controlling the fluid preparation section—the control unit may be configured to verify if said measurement task is under execution. If the verification confirms that measurement task is under execution, the control unit waits for termination at least said upstream variation to the conductivity, or to the concentration for at least one substance ($Cd_{in}$), in the fresh treatment liquid with respect to said prescription baseline, before allowing any other control procedure, e.g. the first control procedure, to adjust the conductivity $C_D$, or the concentration of at least one substance $Na_D$, in the fresh dialysis liquid flowing in the dialysate. This provision allows a more reliable measure of Cb.

Here below it is now described how each of the first and second control procedure may work in term of the algorithm used for determining the control values (step 102c in FIG. 4; blocks 102c', 102c'' in FIG. 3) of the parameters used for adjusting the ultrafiltration and respectively the composition of the dialysis liquid.

The first control procedure comprises determining at instant t at least a first error parameter $ERR\_BV\_UF_{(t)}$ (step 102b) on the basis of the difference between the measured value of the first parameter $BV\ \%_{mes(t)}$ at the control instant t and the corresponding prescription value for the same first parameter $BV\ \%_{traj(t)}$, and on the difference between a measured value of the second parameter $UF_{mes(t)}$ or $WL_{mes(t)}$ cumulated at the instant t and a corresponding prescription value for the same second parameter $UF_{traj(t)}$ or $WL_{traj(t)}$. The first control procedure provides for controlling the ultrafiltration through said membrane at instant t ($UFR_{(t)}$), by acting on the ultrafiltration device 20, at least based on the value of said first error parameter and on the value imposed to the ultrafiltration rate at a previous control instant ($UFR_{(t-\Delta t)}$:

$$UFR_{(t)}=f(UFR_{(t-\Delta t)};ERR\_BV\_UF_{(t)})$$

The second control procedure comprises determining at least a second error parameter $ERR\_BV\_Na_{(t)}$ (step 102b) on the basis of the difference between the value of the third parameter $Cd_{mes(t)}$ at instant t and a corresponding prescription value for the same third parameter $Cb_{traj(t)}$, and the difference between the measured value of the first parameter $BV\ \%_{mes(t)}$ and a corresponding prescription value for the same first parameter $BV\ \%_{traj(t)}$. Then the second control procedure provides for controlling the fluid preparation section to adjust at time instant t the conductivity $C_D$, or the concentration of at least one substance $Na_D$, in the fresh dialysis liquid flowing in the dialysate line, at least based on the value of said second error parameter and on the value imposed to conductivity or concentration in the dialysis liquid at a previous control instant ($Na_D(t-\Delta t)$):

$$Na_D=f(Na_{D(t-\Delta t)};ERR\_BV\_Na_{(t)})$$

Finally, in accordance with a further aspect of the invention which is particularly useful when the apparatus includes at least one infusion line (e.g. line 9 or lines 9a, 9b) configured for the infusion of a replacement fluid and connected to the extracorporeal circuit, the control unit may be further configured to execute a TMP setting procedure (see FIGS. 5 and 6) comprising:
  receive measured values of a fourth parameter (UFR; $Q_{INF}$) related to the ultrafiltration rate through the membrane or to the infusion rate through said infusion line and measured values of a fifth parameter related to the transmembrane pressure (TMP) across said membrane;

impose on a first value of the first parameter ($TMP_n$) a first increase ($\delta TMP_n$) such as to reach a second transmembrane pressure value ($TMP_{n+1}$);

determine a variation between the value of the fourth patameter ($\Delta UFR_{(n)}$; $\Delta Q_{INF(n)}$) measured at the first transmembrane pressure ($TMP_n$) and the value of the fourth patameter ($\Delta UFR_{(n+1)}$ $Q_{INF(n+1)}$) measured at the second transmembrane pressure value ($TMP_{n+1}$);

compare the fourth parameter value variation ($\Delta UFR_{(n)}$; $\Delta Q_{INF(n)}$) with a reference value and, if the value of said variation is greater than the reference value, imposing a second increase ($\delta TMP_{n+1}$) on the second transmembrane pressure in order to reach a third value of the transmembrane pressure value $TMP_{n+2}$;

repeating the above steps of the TMP setting procedure until a maximum or substantially maximum TMP value is reached;

setting said TMP maximum or substantially TMP maximum or a predetermined fraction thereof as set value for the TMP in the course of at least a time interval during treatment.

The above setting procedure is performed if it is intended to control the apparatus also on the basis of the TMP and for example to maximise as much as possible the infused fluid volume, thus increasing the convective exchange. The setting procedure is performed at a setting instant indicated by τ and possibly repeated a plurality of times during a treatment. For example the setting procedure may be performed while one or both the control procedures is/are performed. For example, the control unit is configured to repeat both the control procedures (at a plurality of control instants t that are temporally consecutive to one another) and the setting procedure of the TMP (at a plurality of control instants t that are temporally consecutive to one another). In practice the control unit may be configured to impose the control value or values determined using the first and second control procedures for a time interval Δt following each control instant t, cyclically repeating the control procedures during the whole treatment. In parallel, the control unit is also configured to perform the setting sequence at a plurality of setting instants τ temporally consecutive to one another, imposing the TMP thus determined.

In more detail with regard to the setting procedure and with reference to an embodiment, the setting procedure comprises the following steps, aimed at identifying an optimal value of TMP at which a maximisation of the ultrafiltration is obtained. By acting on the pump 13, the control unit determines a first increase $\delta TMP_n$ to reach a second transmembrane pressure value $TMP_{n+1}$; then the sequence comprises measuring or calculating a variation $\Delta UFR_{(n)}$ between the ultrafiltration flow UFR across the membrane 5 at the first transmembrane pressure $TMP_n$ and the ultrafiltration flow UFR at the second transmembrane pressure $TMP_{n+1}$: the variation of the ultrafiltration flow is determined either by direct measuring of the ultrafiltration flow or indirectly by taking account of both the flow variations of the replacement liquid $\Delta Q_{INF(n)}$ along the infusion line and the variations of weight loss rate $\Delta WLR_{(n)}$ due to the control procedure. Following this the control sequence comprises comparing the ultrafiltration variation $\Delta UFR_{(n)}$ with a reference value and, if the variation value $\Delta UFR_{(n)}$ is greater than the reference value, commanding the pump 13 to impose a second increase $\delta TMP_{n+1}$ on the transmembrane pressure in order to reach a third transmembrane pressure value $TMP_{n+2}$, and so on, cyclically repeating the described sequence for successive increases. The ultrafiltration flow rate variation ΔUFR is compared with a reference flow rate, for example 3 ml/min and, should the ultrafiltration flow rate be greater than 3 ml/min, the ultrafiltration pump 13 is commanded such as to set an increase of TMP that is greater than the preceding one. In this way, if following the first TMP variation the corresponding variation in ultrafiltration flow rate is sufficiently high and therefore such as to indicate that the treatment unit is operating in a sufficiently distant zone from the plateau zone (with reference to the characteristic Ultrafiltration/TMP curve relating to the treatment unit), the above-described sequence is repeated, newly increasing the TMP. Note that, for example, the control unit may considerably increase the amplitude of the following pressure increase, in this way accelerating the search for and the setting of the optimal TMP. If on the other hand the value of the variation ΔUFR of the ultrafiltration flow is lower than the reference value, the TMP setting procedure is interrupted, as will be more fully described herein below, as the unit in this case considers that it has reach the optimal TMP and thus maintains it as the set value.

Figure 5:
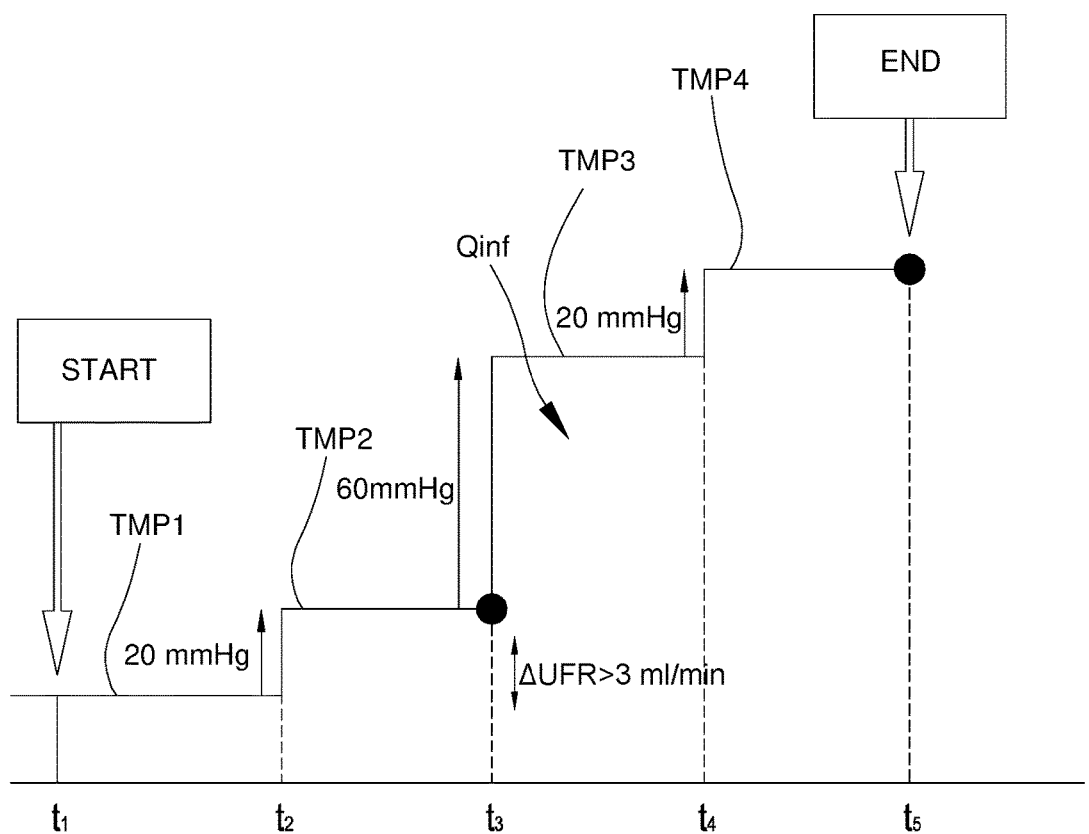
FIG. 5 is a time chart showing a setting procedure according to an aspect of the invention, which may be carried out by the control unit of an apparatus for example of the type illustrated in FIG. 1 and FIG. 2, during or after performance of the control procedure of FIG. 4.

FIG. 5 shows a system of Cartesian axes in which the x-axis represents the time and the y-axis the TMP pressure the pressure TMP set instant by instant: FIG. 5 shows an embodiment of a sequence of TMP setting that may be performed by a control unit which is part of the apparatus 1 of the type illustrated in FIG. 1 or FIG. 2. Following a manual command or an automatic procedure, a TMP setting procedure is started by the control unit. At first (START in FIG. 5), the control unit maintains the TMP at a value of $TMP_1$ for a first time interval $t_1$-$t_2$. At the end of the first time interval $t_1$-$t_2$, a pressure increase of 20 mmHg is imposed on the set TMP value, passing to a set value of $TMP_2$, with a consequent activation of the ultrafiltration pump 13 and the infusion pump 16 (or at least one of the pumps 16a, 16b in the case of FIG. 2). If, in interval $t_2$-$t_3$, the variation in ultrafiltration flow rate ΔUFR is greater than 3 ml/min, for example 12 ml/min, the successive increase in the set value of TMP is optionally imposed at greater than 20 mmHg and, in the illustrated example, at 60 mmHg. Note that in the meantime if the control procedure performed during the setting has varied the weight loss rate WLR the control unit would take account of it in evaluating the effective rise in ultrafiltration at each TMP rise: either the variation ΔUFR is measured directly or, if the variation is calculated on the basis of the variation in the infusion flow, the eventual contribution given by the flow variation of weight loss WLR is added to the infusion flow. In response to the new set value of TMP, i.e. $TMP_3$, the control unit also commands the acceleration of the infusion pump such as to balance the effect of the greater ultrafiltration. Note also that the duration of the interval $t_3$-$t_4$ is not necessary equal to that of the interval $t_2$-$t_3$: for example the unit 15 may be configured to impose a variable interval, which becomes greater as a function with the increment in TMP that precedes it, with the aim of enabling a transitory of adaptation for the ultrafiltration pump and the infusion pump or pumps. Still with reference to FIG. 5, at instant $t_4$ a new TMP increase is imposed, 20 mmHg, and after a further interval T (in FIG. 5: $t_4$-$t_5$), the increase in the ultrafiltration flow is verified. If, as in the illustrated case, the variation in flow rate ΔUFR is less than 3 ml/min, the setting sequence is considered to be concluded ("END" in FIG. 5) and the final TMP value reached (i.e. $TMP_4$ in FIG. 5) is imposed as set value. Otherwise, a new TMP increase is imposed, which may be again of 20 mmHg or may be a function of the variation measured ΔUFR in ultrafiltration flow UFR.

Figure 6:
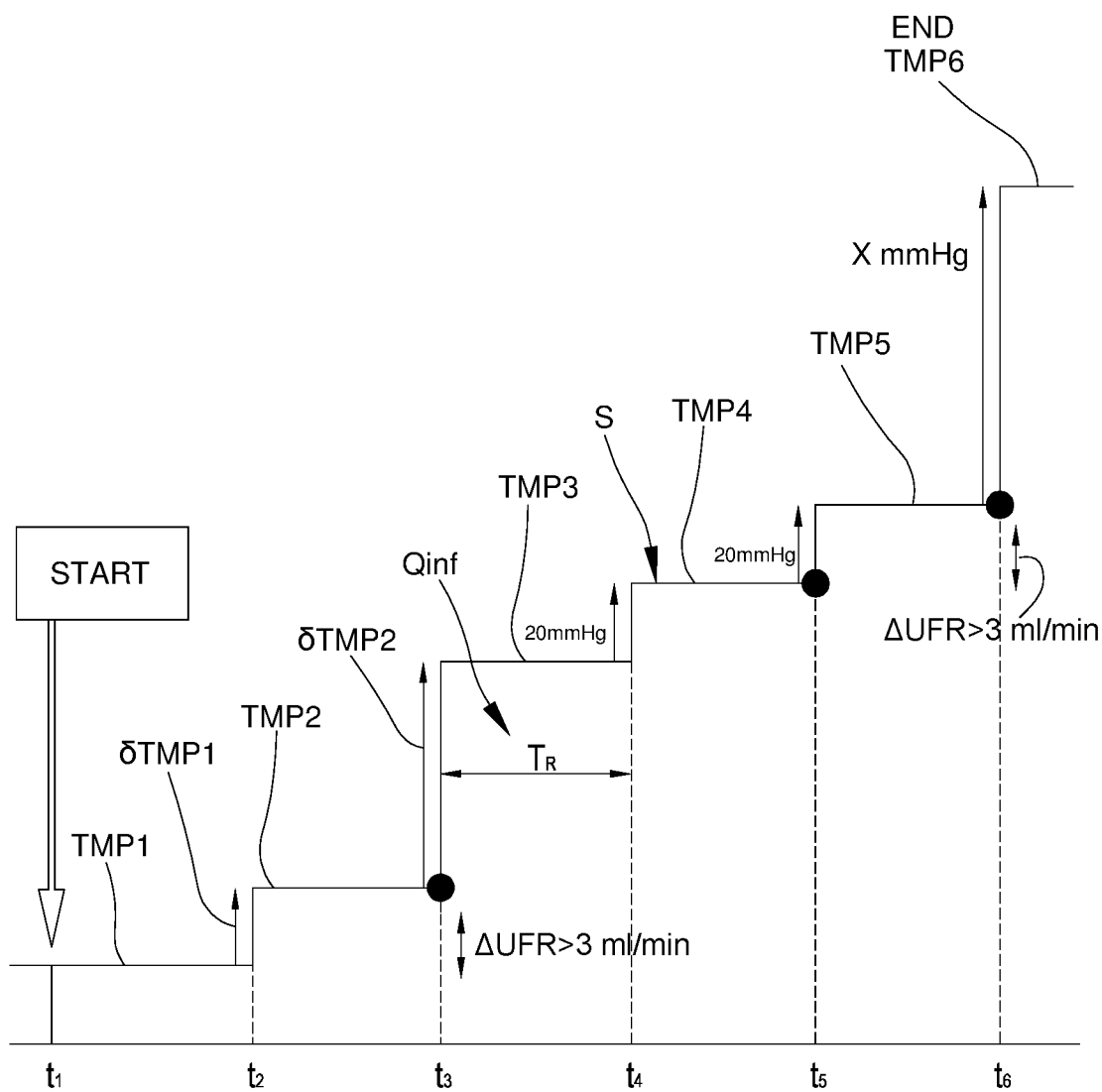
FIG. 6 is a time chart showing the progression of the transmembrane pressure TMP during setting of the TMP, in an aspect of the invention.

FIG. 6 illustrates a situation in which the above-described steps are repeated up to reaching pressure $TMP_3$; thereafter, the setting process may comprise the TMP variation in one or two steps of predetermined entity with the aim of enabling stabilisation of the control system. The TMP variation or variations are kept lower than or equal to a relatively low value, for example 20 mmHg. For example, FIG. 6 shows a stabilizing step, denotes by s. After a further time interval $t_4$-$t_5$, the sequence repeats the previously-described steps with reference to intervals from $t_2$ to $t_4$. In other words, at instant $t_5$, a pressure increment of 20 mmHg is imposed on the value of the TMP passing to a set value $TMP_5$ with a consequent activating of the ultrafiltration pump 13 and the infusion pump 16 (or at least one of the pumps 16a, 16b in the case of FIG. 2) such as to balance the effect of the greater ultrafiltration. If, as in FIG. 6, in interval $t_5$-$t_6$, the variation $\Delta UFR$ in ultrafiltration flow rate UFR is above 3 ml/min, for example 12 ml/min, the successive increment of the TMP set value is imposed at greater than 20 mmHg and, in the illustrated example, at 60 mmHg. In response to the new set value of TMP ($TMP_6$), the control unit also commands acceleration of the infusion pump such as to balance the effect of the greater ultrafiltration, according to one of the above-described control strategies. Then, a new TMP increase of 20 mmHg will be imposed and after a further interval T, the increase in the ultrafiltration flow rate $\Delta UFR$ will be verified. If in response the UFR varies by a value $\Delta UFR$ that is lower than 3 ml/min, the setting sequence is considered to be concluded. Otherwise, the described process is newly reiterated. In general, the setting process comprises that at the start a TMP increase with a predetermined value is imposed, which may be the same or may vary during treatment, but is known a priori and is normally relatively small, for example 20 mmHg. Increases after the first ($\delta TMP_{n+1}$) are either stabilizing increases as described above, and therefore also of 20 mmHg or known and relatively small values, or TMP values calculated in accordance with the measured or estimated ultrafiltration variation value $\Delta UFR$ corresponding to the rise in immediately-preceding transmembrane pressure ($\delta TMP_n$), or rises in TMP that are always constant and of known amplitude a priori. The preceding stages are repeated up to when, following a pressure step, the variation in ultrafiltration flow rate satisfies the end condition of the sequence: at this point, the control unit is configured such as to command the regulating device 20, setting, as operating transmembrane pressure, the last pressure at which the value of the control parameter is less than the value of the respective reference value. If during the performing of the transmembrane setting procedure there is a modification in the weight loss rate, e.g. due to the intervening of the first control procedure (this may happen as the control procedure is repeated quite frequently), the setting sequence involves two actions. Firstly the variation in the ultrafiltration flow rate, if estimated as a function of the variation in the infusion rate, takes account of any variation in the weight loss rate, i.e. in each time interval $t_n$-$t_{n+1}$ (see FIGS. 5 and 6 for example) the variation $\Delta UFR$ is calculated as $\Delta Q_{INF}+\Delta WLR$.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

The invention claimed is:

1. An apparatus for extracorporeal blood treatment, comprising:
    at least a treatment unit having at least a first chamber and at least a second chamber separated from one another by a semipermeable membrane;
    at least a blood removal line connected to an inlet port of the first chamber and configured to remove blood from a patient;
    at least a blood return line connected with an outlet port of the first chamber and configured to return treated blood to the patient, the blood removal line, the blood return line and the first chamber part of an extracorporeal blood circuit;
    a dialysate circuit comprising:
    at least a dialysis line connected to the inlet port of the second chamber and configured to convey fresh dialysis liquid to the second chamber,
    at least a fluid evacuation line connected to an outlet port of the second chamber and configured to discharge spent dialysis liquid exiting from the second chamber, and
    a fluid preparation section connected to the dialysis line and configured for adjusting the dialysis liquid conductivity, or the dialysis liquid concentration for at least one substance, in the fresh dialysis liquid;
    at least one ultrafiltration device connected to the dialysate circuit and configured for causing ultrafiltration of fluid through the membrane from the first to the second chamber; and
    a control unit connected to the ultrafiltration device and to the fluid preparation section and programmed to perform a first control procedure comprising:
    receiving measured values of:
    a first parameter (BV $\%_{mes(t)}$) relating to the change of blood volume in the blood circulating in the extracorporeal blood circuit between start of the treatment and a respective treatment time instant (t), and
    a second parameter related to the amount of ultrafiltration volume ($UF_{mes(t)}$; $WL_{mes(t)}$) cumulated until treatment time instant (t) from the start of the treatment;
    receiving prescription values of the first parameter (BV $\%_{traj(t)}$), and of the second parameter ($UF_{traj(t)}$; $WL_{traj(t)}$) which have to be reached in the patient at treatment time instant (t); and
    controlling the ultrafiltration of fluid through said membrane, by acting on the ultrafiltration device, at least based on the measured values of the first and second parameters and on the prescription values of the same first and second parameters;
    the control unit also programmed to perform a second control procedure comprising:
    receiving a measured value of a third parameter ($Cb_{mes(t)}$) related to the blood conductivity, or to the blood concentration for at least one substance, in the blood circulating in the extracorporeal blood circuit at the respective treatment time instant (t), wherein the step of receiving the measured value of the third parameter comprises comparing one or more measured values of the conductivity or the concentration of at least one substance in the spent dialysis liquid flowing in the spent dialysis line with one or more value of the conductivity or concentration of at least one substance in the fresh dialysis liquid;
    receiving a prescription value of the third parameter ($Cb_{traj(t)}$) to be reached in the patient at the time instant (t); and controlling the fluid preparation section to adjust the dialysis liquid conductivity ($C_D$), or the dialysis liquid concentration of at least one substance ($Na_D$), in the fresh dialysis liquid flowing in the dialysis line at least based on said measured value ($Cb_{mes(t)}$) and on said prescription value for the third parameter ($Cb_{traj(t)}$).

2. The apparatus of claim 1, wherein the step of receiving a measured value of the third parameter ($Cb_{mes(t)}$) comprises commanding execution of a measurement task comprising the following steps:
  causing fresh dialysis liquid to flow in the dialysis line to the second chamber with the dialysis liquid conductivity, or to the dialysis liquid concentration for at least one substance, being at a baseline ($Cd_{set}$) set value which is either constant or varying in a known manner over time;
  causing spent dialysis liquid to flow out of the second chamber into the fluid evacuation line;
  causing an upstream variation to the dialysis liquid conductivity, or to the dialysis liquid concentration for at least one substance, ($CD_{in}$) in the fresh dialysis liquid with respect to said prescription baseline thereby causing a corresponding and timely delayed downstream variation to the dialysis liquid conductivity, or to the dialysis liquid concentration for at least one substance, ($Cd_{out}$) in the spent dialysis liquid flowing in the fluid evacuation line;
  measuring one or more values taken by said downstream variation of the dialysis liquid conductivity, or of the dialysis liquid concentration for at least one substance ($Cd_{out}$), in the spent dialysis liquid;
  determining the measured value of the third parameter ($Cb_{mes(t)}$) related to the blood conductivity, or to the concentration for at least one substance in the blood, by comparing said one or more measured values taken by said downstream variation with one or more values taken by said upstream variation.

3. The apparatus of 1, wherein the control unit is programmed to repeat the first control procedure and the second control procedure at a plurality of regular time intervals during treatment so as to match, as closely as possible, the measured values of said first, second and third parameters to the respective prescription values.

4. The apparatus of claim 1, wherein the control unit is programmed to repeat the first control procedure either as frequently as, or more frequently than, the second control procedure.

5. The apparatus of claim 2, wherein the control unit is programmed to repeat the first control procedure at least once every n minutes, and to repeat the measurement task and the second control procedure no more than once every m minutes, with n being an integer<than ½ m, optionally wherein n is between 1 and 5 and m is between 10 and 30.

6. The apparatus of claim 2, wherein the control unit is programmed to repeat the measurement task less frequently than the first control procedure thereby receiving the measured values of the third parameter ($Cb_{mes(t)}$) less frequently than the measured values (BV $\%_{mes(t)}$, $UF_{mes(t)}$; BV $\%_{mes(t)}$, $WL_{mes(t)}$) of the first and second parameters, and
  wherein the control unit is further programmed to estimate values taken by the third parameter at time instants intermediate between two consecutive executions of the measurement task at least based on:
    a mathematical model (M), representing kinetics of the solutes in a distribution volume in the patient, and
    the measured values of the third parameter made at said two consecutive measurement tasks,
  thereby obtaining a plurality of estimated values of the third parameter between each two consecutive actually measured values of the same third parameter.

7. The apparatus of claim 2, wherein the second control procedure comprises receiving the measured value of the first parameter (BV $\%_{mes(t)}$) relating to the change of blood volume in the blood circulating in the extracorporeal blood circuit between start of the treatment and treatment time instant (t), and receiving the prescription value of the first parameter (BV $\%_{traj(t)}$) to be reached in the patient at treatment time instant (t); wherein the controlling step in the second control procedure comprises controlling the fluid preparation section to adjust the dialysis liquid conductivity ($C_D$), or the concentration of at least one substance ($Na_D$), in the fresh dialysis liquid flowing in the dialysis line at least based on the measured values of the first and third parameters (BV $\%_{mes(t)}$; $Cb_{mes(t)}$) and on the prescription values of the first and third parameters (BV $\%_{traj(t)}$; $Cb_{traj(t)}$).

8. The apparatus of claim 7, wherein, during execution of said step of controlling the fluid preparation section, the control unit is programmed to:
  verify if said measurement task is under execution, and
  in the affirmative, wait for termination of at least said upstream variation to the dialysis liquid conductivity, or to the concentration for at least one substance ($Cd_{in}$), in the fresh dialysis liquid with respect to said prescription baseline, and only then allow the second control procedure to adjust the dialysis liquid conductivity, or the dialysis liquid concentration of at least one substance, in the fresh dialysis liquid flowing in the dialysis line.

9. The apparatus according to claim 8,
  wherein the control unit is programmed to repeat the measurement task less frequently than the first control procedure thereby receiving the measured values of the third parameter ($Cb_{mes(t)}$) less frequently than the measured values (BV $\%_{mes(t)}$, $UF_{mes(t)}$; BV $\%_{mes(t)}$, $WL_{mes(t)}$) of the first and second parameters,
  wherein the control unit is further programmed to estimate values taken by the third parameter at time instants intermediate between two consecutive executions of the measurement task at least based on:
    a mathematical model (M), representing kinetics of the solutes in a distribution volume in the patient, and
    the measured values of the third parameter made at said two consecutive measurement tasks,
    thereby obtaining a plurality of estimated values of the third parameter between each two consecutive actually measured values of the same third parameter; and
  wherein the values of the third parameters used as measured values in the second control procedure include measured values obtained with execution of said measurement task and estimated values relating to time instants intermediate between two consecutive executions of the measurement task.

10. The apparatus of claim 2, wherein the control unit is programmed to:
  receive a value for total treatment time (T);
  receive prescription values of blood volume variation (BV $\%_{target}$), weight loss ($WL_{target}$) and blood conductivity or concentration for at least one substance in blood ($Cb_{target}$) to be reached at end of treatment time (T); and
  determine said prescription values of the first parameter (BV $\%_{traj(t)}$), of the second parameter ($UF_{traj(t)}$; $WL_{traj(t)}$) and of the third parameter ($Cb_{traj(t)}$) on the basis of the respective prescription values to be reached at the end of the treatment and on the treatment time value (T).

11. The apparatus of claim 10, wherein receiving a prescription of the blood conductivity, or concentration for at least one substance in blood, ($Cb_{target}$) to be reached at end of treatment time (T) comprises imposing that said prescription value of blood conductivity or concentration for at least one substance in blood ($Cb_{target}$) to be reached at end of treatment time (T) shall be equal to the value of the blood conductivity or concentration for at least one substance in blood at the beginning of the treatment as measured or as set by a user.

12. The apparatus of claim 11, wherein the control unit is programmed to execute the measurement task at the beginning of the treatment to measure the value of the blood conductivity, or concentration for at least one substance in blood, at the beginning of the treatment.

13. The apparatus of claim 1, wherein the first control procedure comprises:
- determining at instant (t) at least a first error parameter ($ERR\_BV\_UF_{(t)}$) on the basis of:
  - the difference between the measured value of the first parameter (BV $\%_{mes(t)}$) at the instant (t) and a corresponding prescription value for the same first parameter (BV $\%_{traj(t)}$), and
  - the difference between a measured value of the second parameter ($UF_{mes(t)}$; $WL_{mes(t)}$) cumulated at the instant (t) and a corresponding prescription value for the same second parameter ($UF_{traj(t)}$; $WL_{traj(t)}$); and
- controlling the ultrafiltration of fluid through said membrane, by acting on the ultrafiltration device, at least based on the value of said first error parameter.

14. The apparatus of claim 1, wherein the second control procedure comprises:
- determining at least a second error parameter ($ERR\_BV\_Na_{(t)}$) on the basis of:
  - the difference between the value of the third parameter ($Cd_{mes(t)}$) at instant (t) and a corresponding prescription value for the same third parameter ($Cb_{traj(t)}$), and
  - the difference between the measured value of the first parameter (BV $\%_{mes(t)}$) and a corresponding prescription value for the same first parameter (BV $\%_{traj(t)}$); and
- controlling the fluid preparation section to adjust the dialysis liquid conductivity ($C_D$), or the dialysis liquid concentration of at least one substance ($Na_D$), in the fresh dialysis liquid flowing in the dialysis line at least based on the value of said second error parameter.

15. The apparatus according to claim 1 further comprising at least one infusion line configured for the infusion of a replacement fluid and connected to the extracorporeal circuit,
wherein the control unit is further programmed to execute a TMP setting procedure comprising:
- receiving measured values of a fourth parameter (UFR; $Q_{INF}$) related to the ultrafiltration rate through the membrane or to the infusion rate through said infusion line and measured values of a fifth parameter related to the transmembrane pressure (TMP) across said membrane;
- imposing on a first value of the first parameter ($TMP_n$) a first increase ($\delta TMP_n$) such as to reach a second transmembrane pressure value ($TMP_{n+1}$);
- determining a variation between the value of the fourth parameter ($\Delta UFR_{(n)}$; $\Delta Q_{INF(n)}$) measured at the first transmembrane pressure ($TMP_n$) and the value of the fourth parameter ($\Delta UFR_{(n+1)}$ $Q_{INF(n+1)}$) measured at the second transmembrane pressure value ($TMPn+1$);
- comparing the fourth parameter value variation ($\Delta UFR_{(n)}$; $\Delta Q_{INF(n)}$) with a reference value and, if the value of said variation is greater than the reference value, imposing a second increase ($\delta TMP_{n+1}$) on the second transmembrane pressure in order to reach a third value of the transmembrane pressure value ($TMP_{n+2}$);
- repeating the above steps of the TMP setting procedure until a maximum or substantially maximum TMP value is reached; and
- setting said TMP maximum or substantially TMP maximum or a predetermined fraction thereof as set value for the TMP in the course of at least a time interval during treatment.

16. The apparatus of claim 1, comprising:
- at least a sensor active on the extracorporeal circuit and configured for detecting the variation (BV %) of the blood volume of the patient blood;
- at least a sensor active at least on the evacuation line and configured for determining the ultrafiltration rate (UFR) across the membrane;
- at least a sensor active on the dialysis line and configured for detecting dialysis liquid conductivity or dialysis liquid concentration for at least one substance (Cd; Na) of the liquid crossing the dialysis line;
- at least a sensor configured for determining an infusion rate ($Q_{INF}$) of the replacement fluid crossing an infusion line; and
- at least a sensor configured for determining a transmembrane pressure (TMP) between the first and the second chamber;
wherein the above sensors are connected to the control unit.

17. The apparatus of claim 1, wherein the first parameter is the change of blood volume in the blood circulating in the extracorporeal blood circuit between start of the treatment and the respective treatment time instant (t).

18. The apparatus of claim 1, wherein the third parameter is the blood conductivity, or the blood concentration for at least one substance, in the blood circulating in the extracorporeal blood circuit at the respective time instant (t) during treatment.

19. The apparatus of claim 15, wherein the fourth parameter is the ultrafiltration rate through the membrane or the infusion rate through said infusion line.

20. The apparatus of claim 2, wherein the control unit is programmed to interdict any intervention on the composition of the dialysis liquid on the part of any task other than the measurement task while the change in conductivity or concentration imposed on the fresh dialysis liquid made by the measurement task is taking place.

21. An apparatus for extracorporeal blood treatment, comprising:
- a treatment unit having at least a first chamber and at least a second chamber separated from one another by a semipermeable membrane;
- a blood removal line connected to an inlet port of the first chamber and configured to remove blood from a patient,
- a blood return line connected with an outlet port of the first chamber and configured to return treated blood to the patient, the blood removal line, the blood return line and the first chamber being part of an extracorporeal blood circuit;

a dialysate circuit comprising:
a dialysis line connected to the inlet port of the second chamber and configured to convey fresh dialysis liquid to the second chamber,
a fluid evacuation line connected to an outlet port of the second chamber and configured to discharge spent dialysis liquid exiting from the second chamber, and
a fluid preparation section connected to the dialysis line and configured to adjust the conductivity, or the concentration for at least one substance, in the fresh dialysis liquid;
an ultrafiltration device connected to the dialysate circuit and configured to determine an ultrafiltration through the membrane from the first chamber to the second chamber;
a control unit connected to the ultrafiltration device and to the fluid preparation section and programmed to perform a first control procedure comprising:
receiving measured values of:
a first parameter (BV $\%_{mes(t)}$) relating to the change of blood volume in the blood circulating in the extracorporeal blood circuit between a start of the treatment and a respective treatment time instant (t), and
a second parameter related to the amount of ultrafiltration volume ($UF_{mes(t)}$; $WL_{mes(t)}$) accumulated until treatment time instant (t) from the start of the treatment,
receiving prescription values for the first parameter (BV $\%_{traj(t)}$), and for the second parameter ($UF_{traj(t)}$; $WL_{traj(t)}$) which are to be reached in the patient at treatment time instant (t); and
controlling the ultrafiltration through said membrane, by acting on the ultrafiltration device, based at least on the measured values of the first and second parameters and on the prescription values of the same first and second parameters;
the control unit being further programmed to perform a second control procedure comprising:
receiving a measured value for a third parameter ($Cb_{mes(t)}$) related to the conductivity or to the concentration for at least one substance in the blood circulating in the extracorporeal blood circuit at the respective treatment time instant (t);
receiving a prescription value for the third parameter ($Cb_{traj(t)}$) to be reached in the patient at the time instant (t);
controlling the fluid preparation section to adjust conductivity ($C_D$), or the concentration of at least one substance ($Na_D$), in the fresh dialysis liquid flowing in the dialysis line based at least on said measured value ($Cb_{mes(t)}$) and on said prescription value for the third parameter ($Cb_{traj(t)}$);
wherein the step of receiving a measured value of the third parameter ($Cb_{mes(t)}$) comprises commanding execution of a measurement task comprising the following steps:
causing fresh dialysis liquid to flow in the dialysis line to the second chamber with the conductivity, or the concentration for at least one substance, being at a baseline ($Cd_{set}$) set value which is either constant or varying in a known manner over time;
causing spent dialysis liquid to flow out of the second chamber into the fluid evacuation line;
causing an upstream variation to the conductivity, or to the concentration for at least one substance ($Cd_{in}$), in the fresh dialysis liquid with respect to said baseline, thereby causing a corresponding delayed downstream variation to the conductivity, or to the concentration for at least one substance ($Cd_{out}$), in the spent dialysis liquid flowing in the fluid evacuation line;
measuring one or more values taken by said downstream variation of the conductivity or concentration for at least one substance ($Cd_{out}$) in the spent dialysis liquid; and
determining the measured value of the third parameter ($Cb_{mes(t)}$) related to the conductivity or to the concentration for at least one substance in the blood, by comparing said one or more measured value taken by said downstream variation with one or more value taken by said upstream variation, and
wherein the control unit is programmed to prevent any intervention on the composition of the fresh dialysis liquid on the part of any task other than the measurement task while the variation in conductivity or concentration imposed on the fresh dialysis liquid made by the measurement task is taking place.

22. The apparatus of the claim 21, wherein the control unit is programmed to repeat the first control procedure and the second control procedure at a plurality of regular time intervals during treatment such as to match, as closely as possible, the measured values of said first, second and third parameters to the respective prescription values.

23. The apparatus of claim 21, wherein the control unit is programmed to repeat the first control procedure as frequently as, or more frequently than, the second control procedure.

24. The apparatus of claim 21, wherein the control unit is programmed to repeat the first control procedure at least once every n minutes, and to repeat the measurement task and the second control procedure no more than once every m minutes, with n being an integer<than ½ m, wherein n is comprised between 1 and 5 and m is comprised between 10 and 30.

25. The apparatus of claim 21, wherein the control unit is programmed to repeat the measurement task less frequently than the first control procedure, thereby receiving the measured values of the third parameter ($Cb_{mes(t)}$) less frequently than the measured values (BV $\%_{mes(t)}$, $UF_{mes(t)}$; BV $\%_{mes(t)}$, $WL_{mes(t)}$) of the first and second parameters, and
wherein the control unit is further programmed to estimate values taken by the third parameter at time instants intermediate between two consecutive executions of the measurement task based at least on:
a mathematical model (M), representing kinetics of the solutes in a distribution volume in the patient, and
the measured values of the third parameter made at said two consecutive measurement tasks,
thereby obtaining a plurality of estimated values of the third parameter between each two consecutive actually measured values of the same third parameter.

26. The apparatus of claim 21, wherein the second control procedure comprises receiving the measured value of the first parameter (BV $\%_{mes(t)}$) relating to the change of blood volume in the blood circulating in the extracorporeal blood circuit between start of the treatment and treatment time instant (t), and receiving the prescription value of the first parameter (BV $\%_{traj(t)}$) to be reached in the patient at treatment time instant (t); wherein the controlling step in the second control procedure comprises controlling the fluid preparation section to adjust the conductivity ($C_D$), or the concentration of at least one substance ($Na_D$), in the fresh dialysis liquid flowing in the dialysis line based at least on the measured values of the first and third parameters (BV $\%_{mes(t)}$; $Cb_{mes(t)}$) and on the prescription values of the first and third parameters (BV $\%_{traj(t)}$; $Cb_{traj(t)}$).

27. The apparatus according to claim 21, wherein, during execution of said step of controlling the fluid preparation section, the control unit is programmed to:
verify if said measurement task is under execution and, in the affirmative, wait for termination of at least said upstream variation to the conductivity, or to the concentration for at least one substance ($Cd_{in}$), in the fresh dialysis liquid with respect to said prescription baseline, and then allow the second control procedure to adjust the conductivity, or the concentration of at least one substance, in the fresh dialysis liquid flowing in the dialysis line.

28. The apparatus of claim 21, wherein the control unit is programmed to:
receive a value for total treatment time (T);
receive prescription values of blood volume variation (BV $\%_{target}$), weight loss ($WL_{target}$) and plasma conductivity or concentration for at least one substance in blood ($Cb_{target}$) to be reached at end of treatment time (T); and
determine said prescription values of the first parameter (BV $\%_{traj(t)}$), of the second parameter ($UF_{traj(t)}$; $WL_{traj(t)}$) and of the third parameter ($Cb_{traj(t)}$) on the basis of the respective prescription values to be reached at the end of the treatment and on the treatment time value (T).

29. The apparatus of claim 28, wherein receiving a prescription of the plasma conductivity or concentration for at least one substance in blood ($Cb_{target}$) to be reached at end of treatment time (T) comprises imposing that said prescription value of conductivity or concentration for at least one substance in blood ($Cb_{target}$) to be reached at end of treatment time (T) shall be equal to the value of the conductivity or concentration for at least one substance in blood at the beginning of the treatment, in particular as measured or as set by a user.

30. The apparatus of claim 29, wherein the control unit is programmed to execute the measurement task at the beginning of the treatment to measure the value of the conductivity or concentration for at least one substance in blood at the beginning of the treatment.

31. The apparatus according to claim 21, further comprising at least one infusion line configured for the infusion of a replacement fluid and connected to the extracorporeal circuit,
wherein the control unit is further programmed to execute a transmembrane pressure (TMP) setting procedure comprising:
receive measured values for a fourth parameter (UFR; $Q_{INF}$) related to the ultrafiltration rate through the membrane or to the infusion rate through said infusion line and measured values for a fifth parameter related to the transmembrane pressure (TMP) across said membrane;
impose on a first value of a first transmembrane parameter ($TMP_n$) a first transmembrane increase ($\delta TMP_n$) such as to reach a second transmembrane pressure value ($TMP_{n+1}$);
determine a variation between the value of the fourth parameter ($\Delta UFR_{(n)}$; $\Delta Q_{INF(n)}$) measured at the first transmembrane pressure ($TMP_n$) and the value of the fourth parameter ($\Delta UFR_{(n+1)}$ $Q_{INF(n+1)}$) measured at the second transmembrane pressure value ($TMP_{n+1}$);
compare the fourth parameter value variation ($\Delta UFR_{(n)}$; $\Delta Q_{INF(n)}$) with a reference value and, if the value of said variation is greater than the reference value, impose a second transmembrane increase ($\delta TMP_{n+1}$) on the second transmembrane pressure in order to reach a third value of the transmembrane pressure value $TMP_{n+2}$;
repeat the above steps of the TMP setting procedure until a maximum or substantially maximum TMP value is reached; and
set said TMP maximum or substantially TMP maximum or a predetermined fraction thereof as set value for the TMP in the course of at least a time interval during treatment.

32. The apparatus of claim 21, comprising:
at least a sensor active on the extracorporeal circuit and configured for detecting the variation (BV %) of the blood volume of the patient blood;
at least a sensor active at least on the fluid evacuation line and configured for determining the ultrafiltration rate (UFR) across the membrane,
at least a sensor active on the dialysis line and configured for detecting conductivity or concentration for at least one substance (Cd; Na) of the liquid crossing the dialysis line;
at least a sensor configured for determining an infusion rate ($Q_{INF}$) of the replacement fluid crossing the infusion line; and
at least a sensor configured for determining a transmembrane pressure (TMP) between the first chamber and the second chamber,
wherein the above sensors are connected to the control unit.

* * * * *